US009072745B2

(12) United States Patent
Yan et al.

(10) Patent No.: US 9,072,745 B2
(45) Date of Patent: Jul. 7, 2015

(54) **USE OF *SALVIA MILTIORRHIZA* COMPOSITION IN PREPARING DRUGS FOR SECONDARY PREVENTION OF CORONARY HEART DISEASE**

(75) Inventors: Xijun Yan, Tianjin (CN); Naifeng Wu, Tianjin (CN); Kaijing Yan, Tianjin (CN); He Sun, Tianjin (CN); Zhixin Guo, Tianjin (CN); Guoguang Zhu, Tianjin (CN); Weiwei Liu, Tianjin (CN); Libin Zhao, Tianjin (CN); Ruizhi Luo, Tianjin (CN)

(73) Assignee: TASLY PHARMACEUTICAL GROUP CO., LTD, Tianjin (CN)

( * ) Notice: Subject to any disclaimer, the term of this patent is extended or adjusted under 35 U.S.C. 154(b) by 0 days.

(21) Appl. No.: 13/813,827

(22) PCT Filed: Aug. 8, 2011

(86) PCT No.: PCT/CN2011/078128
§ 371 (c)(1),
(2), (4) Date: Mar. 11, 2013

(87) PCT Pub. No.: WO2012/016549
PCT Pub. Date: Feb. 9, 2012

(65) Prior Publication Data
US 2013/0196005 A1     Aug. 1, 2013

(30) Foreign Application Priority Data
Aug. 6, 2010  (CN) .......................... 2010 1 0253344

(51) Int. Cl.
| *A61K 36/258* | (2006.01) |
| *A61K 36/185* | (2006.01) |
| *A61K 36/537* | (2006.01) |
| *A61K 31/616* | (2006.01) |
| *A61K 45/06*  | (2006.01) |
| *A61K 31/045* | (2006.01) |

(52) U.S. Cl.
CPC ............ *A61K 36/537* (2013.01); *A61K 31/616* (2013.01); *A61K 36/258* (2013.01); *A61K 45/06* (2013.01); *A61K 31/045* (2013.01)

(58) Field of Classification Search
CPC .. A61K 2300/00; A61K 36/258; A61K 36/53
USPC ......................................... 424/408, 728, 773
See application file for complete search history.

(56) References Cited

U.S. PATENT DOCUMENTS

| 4,007,204 A * | 2/1977 | Descamps et al. ............... 549/57 |
| 7,438,935 B2 | 10/2008 | Wei et al. |
| 2002/0098249 A1* | 7/2002 | No ................................. 424/739 |
| 2003/0152651 A1* | 8/2003 | Yan et al. ....................... 424/728 |

FOREIGN PATENT DOCUMENTS

| CN | 1348815 A | 5/2002 |
| CN | 1785249 A | 6/2006 |
| WO | 02/058625 A2 | 8/2002 |

OTHER PUBLICATIONS

Extended European Search Report dated Nov. 15, 2013 for corresponding European Patent Application No. 11 81 4132.
"Advantages of Compound Danshen Dripping Pills in community prevention and cure of coronary heart disease", Contemporary Medicine, Apr. 2009, p. 152, vol. 15—issue No. 10. (Abstract—English Translation).
"Effects of Compound Danshen Dripping Pills on vascular endothelial functions of AMI patients with normal coronary angiography", Shandong Medical Journal, Mar. 2002, pp. 94-95, vol. 49—issue No. 21. (Abstract—English Translation).
"Comparison of therapeutic effects of Compound Danshen Dripping Pills and Tablets in treating coronary heart disease and angina pectoris", Practical Clinical Journal of Integrated Traditional Chinese and Western Medicine, Apr. 2003, pp. 7-8, vol. 3—issue No. 2. (Abstract—English Translation).
"Clinical observation of compound Danshen Dripping Pills preventing restenosis in patients with coronary heart disease after stenting operation", China Medical Herald, Mar. 2009, pp. 68-69, vol. 6—issue No. 9. (Abstract—English Translation).
International Search Report dated Nov. 10, 2011, based on International Application Number: PCT/CN2011/078128.
Office Action mailed on May 7, 2014, by the Patent Office of Japan for the corresponding Japanese Application No. 2013-523481.
"A Phase II, Double Blind, Placebo-controlled, Randomized, Multi-Center, Parallel Group Study to Evaluate the Efficacy and Safety of T89 in Patient With Chronic Stable Angina Pectoris", NCT00797953, Jan. 14, 2010, accessed from http://clinicaltrials.gov/archive/NCT00797953/2010_01_14, National Library of Medicine, pp. 1-4.
Office Action mailed on Jul. 7, 2014, by the Patent Office of Taiwan for the corresponding Taiwanese Application No. 100129936.

\* cited by examiner

*Primary Examiner* — Chris R Tate
*Assistant Examiner* — Randall Winston
(74) *Attorney, Agent, or Firm* — Pergament Gilman & Cepeda LLP; Milagros A. Cepeda; Edward D. Pergament

(57) ABSTRACT

Provided is the use of a *Salvia Miltiorrhiza* composition in preparing drugs for secondary prevention of coronary heart disease, and particularly the use of the *Salvia Miltiorrhiza* composition in preparing drugs for secondary prevention of stable angina type coronary heart disease and the reduction of serious vascular events.

28 Claims, 17 Drawing Sheets

Figure 1:
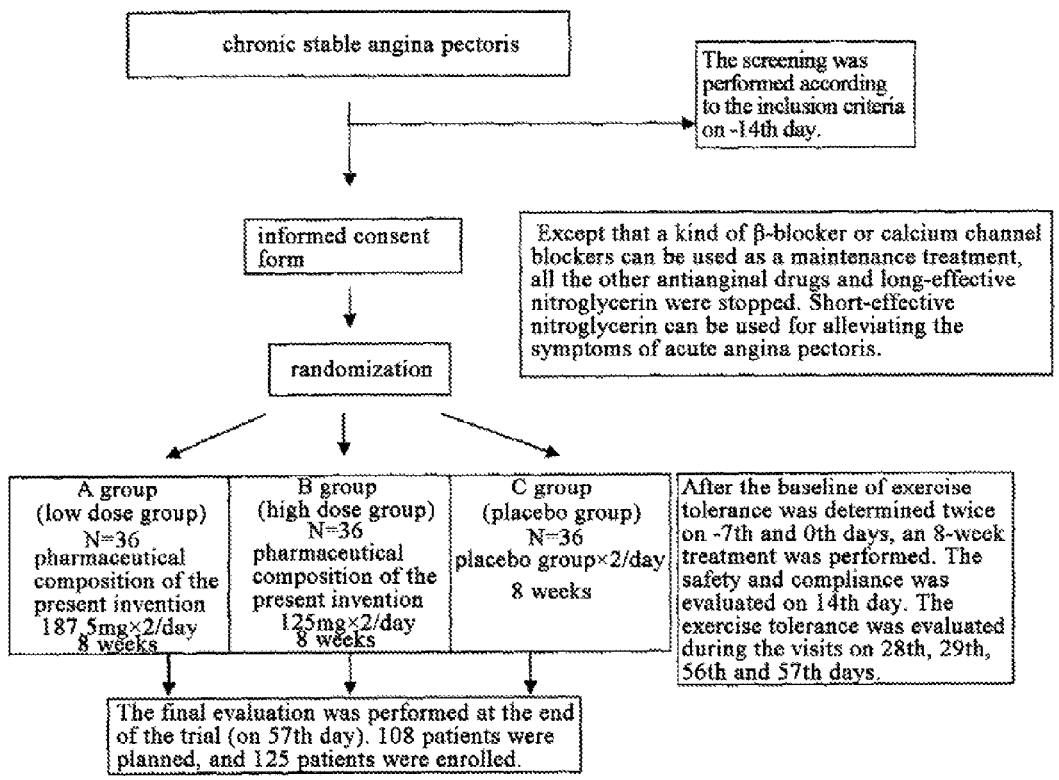

USE OF *SALVIA MILTIORRHIZA* COMPOSITION IN PREPARING DRUGS FOR SECONDARY PREVENTION OF CORONARY HEART DISEASE

This application is a National Stage Application under 35 U.S.C. 371 of PCT International Application No. PCT/CN2011/078128, filed Aug. 8, 2011, which claims priority to Chinese Application 201010253344.5, filed on Aug. 6, 2010; all of which are hereby incorporated by reference in their entirety.

FIELD OF THE INVENTION

The present invention relates to a use of compound drugs in preparing medicine for prevention of coronary heart disease (CHD), in particular to a use of traditional Chinese compound medicine in preparing medicine for prevention of the CHD.

BACKGROUND OF THE INVENTION

Coronary atherosclerotic heart disease (CAHD) refers to a sort of heart disease, which is caused by vascular stenosis or vascular obstruction due to the coronary atherosclerosis, or (and) by myocardial ischemia hypoxia or myocardial necrosis due to the coronary artery function changes (e.g. spasm). All of these are together called as the coronary heart disease (abbr. as CHD), also called as the ischemic heart disease. The CAHD is known as the most common type of atherosclerosis-induced organ pathology, which has also been a common disease seriously doing harm to human health.

Generally, the CHD is caused by coronary atherosclerosis. The onset of the CHD rises with age increase. The older the patients are, the more severe the diseases get. As confirmed by some data, since age of 40, possibilities of the CHD are increased by 1 time with each additional 10 years of age. There has a more rapid development of the coronary atherosclerosis in man after the age of 50, or in woman after 60. In the same way, risk of myocardial infarction is increased with the growth of age. In recent years, onset age of the CHD showed a low-age tendency. Now, the percentage of young people under the age of 35 suffering from the CHD is on the rise, and the youngest patent was only 20 years old. Due to its high incidence and high mortality, the CHD has become a disease threatening human health seriously. So it is called as the "first human killer". Because none of symptoms can be in the least observed before the onset of the CHD, the consequence of some patents would be incredibly bad without timely emergency treatment. Accordingly, in terms of the CHD, prevention is more important than treatment.

Usually, the prevention of CHD includes the primary prevention, secondary prevention and triple prevention. Said primary prevention is targeted to the risk population who has not yet suffered from the CHD; the secondary prevention is to the patients who have been at the early stage of CHD; and the triple prevention is to prevention of occurrence of CHD progression and complications. In practice, prevention has become very important to both the CHD patients and CHD high risk population. Secondary prevention of the CHD refers to early discovery, diagnosis and treatment on the CHD patients. The objective of secondary prevention is focused on ameliorating symptoms, preventing deterioration of the disease, improving prognosis and keeping off the reoccurrence of the CHD. At present, there are two main measures used for the secondary prevention of CHD, the one is to find and control the risk factors; and another is the reliable and continuous drug therapy.

Prevention of the CHD should be comprehensively focused on various factors, including diet, exercise, medication, and controlling risk factors etc. Especially for the CHD patients, the objective of prevention is to ameliorate symptoms of disease, prevent its progress, and keep off its reoccurrence. Prevention of the CHD includes two "ABCDE"s, which take place at each stage of the disease. Only by insisting on the secondary prevention, the treatment is effectively targeted to the etiology with effective reduction of reoccurrence.

Of the first "ABCDE" of the secondary prevention of the CHD, "A" represents aspirin whose main effect is to prevent the formation of atherosclerosis by resisting platelet aggregation and release and improving the balance of prostaglandin and thromboxane A2. In clinic, routine administration of aspirin enteric-coated tablets, 100 mg daily, can prevent the reoccurrence of the CHD. The "B" represents hypertension, which can not only accelerate the speed of progression in atherosclerosis, but also increase its extent. The higher the blood pressure, the greater possibility of occurrence or reoccurrence of the CHD. Effectively reducing blood pressure may prevent the reoccurrence of the CHD. The "C" represents hyperlipidemia. On the one hand, the hyperlipidemia decreases the amount of blood supply in brain by making the blood viscous and slowing the blood-flow; on the other hand, it damages the vascular endothelium to such a degree that it is deposited on the vascular wall to form atherosclerotic plaque. All of these directly cause the occurrence and development of cardiovascular and cerebrovascular diseases. The "D" represents diabetes. More than 80% of diabetes results in abnormal lipid metabolism, which is often accompanied by cardiovascular and cerebrovascular diseases, e.g. the atherosclerosis and hyperlipidemia. Meanwhile, escalated glucose content in blood makes the blood viscosity and coagulation increased, rendering the diabetics very prone to develop the CHD. The "E" represents rehabilitation education. Popularity of education of hypertension, CHD and atherosclerosis prevention should be strengthened by the network publicity, free distribution of readings and regular rehabilitation instruction. By means of active intervention of risk factors, the patients are willing to accept the long-term prevention measures patiently, and active with drug treatment.

Of the second "ABCDE" of the secondary prevention of the CHD, "A" represents active physical exercise. Not only can the proper exercise increase fat consumption, but also reduce deposition of cholesterol in body and improve insulin sensitivity. It is helpful in following aspects: preventing obesity, controlling body weight, increasing circulation function, regulating blood lipid, decreasing blood pressure and reducing thromboses, which is known together as the active measures to prevent the CHD. Strenuous exercise is not suitable for patients, e.g. sprints and climbing. Aerobic exercise is recommended, e.g. jogging, walking, calisthenics and Tai Chi. "B" represents weight control. The BMI should be maintained or lost in the range of 18.5~24.9 kg/m$^2$ and waist circumstance less than 90 cm. "C" represents smoking cessation. Reportedly, there are more 3000 kinds of harmful substances in cigarettes. If the nicotine in smoke is inhaled into the body, it can stimulate the autonomic nervous, make the blood vessel convulsed, quicken the heartbeat, increase the blood pressure and blood cholesterol, thus accelerating atherosclerosis. "D" represents reasonable diet. The food should be varied and cereal-based. The dietary recommended for the patients is present as follows: more magnesium-rich food, e.g. grains, nuts and seaweed; more cellulose-rich food, e.g. vegetables, bananas and potatoes; milk, beans or other products daily; a proper amount of eggs and lean meat often;

and less fat meat, pork skin, hooves and meat dishes. Food intake and physical activity should be kept balanced, and a proper body weight maintained. Food should be salt and sugar-less, and amount of salt is reduced to 6 g a day. "E" represents emotional stability. Optimistic and stable emotion together with comfortable and balanced state of mind is important factors not only in preventing cardiovascular and cerebrovascular disease, but also keys and secrets to long life.

Clinically, the CHD is divided into five types in accordance with its site and scope, degree of vascular occlusion and the development speed, scope and degree of myocardial ischemia. 1. Latent CHD, also known as symptomless CHD, refers to those patients whose ECG, although showing no symptoms, have displayed changes of myocardial ischemia of ST-segment depression, reduced, flattened or inverted T-wave after resting or cardiac stress test. 2. Angina pectoris CHD refers to those patients who suffer from paroxysmal retrosternal pain caused by transient myocardial ischemia. 3. Myocardial infarction CHD has severe symptoms due to the myocardial ischemic necrosis caused by coronary artery occlusion. 4. Heart failure and arrhythmia CHD show symptoms of cardiac enlargement, heart failure and arrhythmia caused by myocardial fibrosis and heart enlargement due to longtime chronic myocardial ischemia. 5. Sudden death CHD always results in sudden death by primary cardiac arrest, which is caused mostly by severe arrhythmia due to electrophysiological disorder locally generated in ischemic myocardium, e.g. ventricular tachycardia and ventricular fibrillation.

At present, β-receptor blocker is mainly used for preventing the Angina pectoris CHD. It works for preventing attack of angina pectoris by decreasing myocardial oxygen consumption under the condition of exercise and tension. Its main contraindication is bronchospasm, bradycardia and decompensated heart failure. Hence, for the patients with asthma or other airway obstructive diseases, the β-receptor blocker would make them worse.

Recently, what have been used for preventing malignant vascular event is mainly focused on antiplatelet agents. They take effect of inhibiting adhesion, aggregation and secretion of platelet through a mechanism of inhibiting arachidonic acid metabolism and increasing cAMP level in platelets. Their main side effect is bleeding. Therefore, they are not used for the patients who suffer from blood coagulation dysfunction or ulcer diseases.

The present invention relates to a compound *Salvia Miltiorrhiza* composition, which has been developed on the basis of both traditional Chinese medicine (TCM) theory and modern pharmacological studies. According to the TCM theory, the pathologic basis of chest stuffiness and heart pain is failure of aiding the blood circulation in heart caused by stagnancy of blood stasis in heart vessel and poor blood circulation. After long-time of pharmacological trials and clinical studies, by means of formula selection, the inventor of present invention has developed aforesaid compound *Salvia Miltiorrhiza* composition having effects of activating blood by removing stasis, stopping pain by relaxing chest stuffiness and resuscitating with aromatic herbs. In this composition, the *Salvia Miltiorrhiza* is used as the monarch drug, *Panax Notoginseng* as the minister drug and *Borneol* as the adjuvant drug. Clinically, it is mainly used for treatment of angina pectoris CHD.

SUMMARY OF THE INVENTION

Objective of present invention is to provide a use of Chinese medicine composition in preparing medicaments for treating secondary prevention of CHD. Said secondary prevention of CHD includes secondary prevention of angina pectoris CHD and reduction of occurrence and reoccurrence of severe vascular events. Said Chinese medicine composition comprises *Salvia Miltiorrhiza* (Danshen) & *Panax Notoginseng* (Sanqi) extract and *Borneol* (Bingpian) in a weight ratio of (8~15):1, wherein weight of *Salvia Miltiorrhiza* (Danshen) & *Panax Notoginseng* (Sanqi) extract is the dry weight.

According to the present invention, said secondary prevention of angina pectoris CHD refers to the secondary prevention of stable angina pectoris CHD. Said Chinese medicine composition has effects of increasing exercise tolerance and prolonging total exercise time in patients with the stable angina pectoris CHD. In addition, said Chinese medicine composition can delay the ST-segment depression or prolong its interval, delay the onset time of angina pectoris or prolong its interval in patients with induced stable angina pectoris CHD, reduce the frequency of angina pectoris, decrease nitroglycerin consumption and improve the life quality in patients with stable angina pectoris CHD. Also, said secondary prevention of stable angina pectoris CHD includes improving the biochemical parameters, as follows: B-type natriuretic peptide (BNP), C-reactive protein (CRP), lipoprotein phospholipase A2 (Lp-PLA2) and homocysteine (HCY). In recent years, a lot of studies showed that BNP, CRP, Lp-PLA2 and HCY participated in the pathogenesis of CHD, and they were likely to be the important factors to lead to local inflammatory reaction in CHD. These biochemical parameters are grown in patients with CHD. As shown in studies of present invention, aforesaid Chinese medicine composition can effectively lower the increased aforesaid biochemical parameters, and there is a statistically significant difference between the biochemical parameters post and pre-treatment ($P<0.01$).

According to the present invention, said Chinese medicine composition may be used in combination with β-receptor blockers in treating secondary prevention of stable angina pectoris CHD. Said β-blockers include, but not limited to, propranolol, pindolol, timolol, metoprolol (Betaloc®) and acebutolol, preferably the Betaloc®. Further, use of said Chinese medicine composition in combination with other or emerging β-receptor blockers should be included within the scope of present invention.

According to the present invention, said reduction of occurrence and reoccurrence of severe vascular event (SVE) especially refers to decreasing occurrence or reoccurrence of severe events, e.g. death, myocardial infarction and ischemia shock etc in the CHD patients. Besides, it includes reducing the need for coronary artery bypass grafting (CAGB), percutaneous transluminal coronary angioplasty (PTCA) and angiocardiography.

According to the present invention, said Chinese medicine composition may be used in combination with antiplatelet agents in reducing occurrence or reoccurrence of severe vascular events. Said antiplatelet agents include, but not limited to, aspirin, acemetacin, troxerutin, dipyridamole, cilostazol, ticlopidine hydrochloride and sodium ozagrel, preferably the aspirin. Further, use of said Chinese medicine composition in combination with other or emerging antiplatelet agents should be included within the scope of present invention.

According to the present invention, said Chinese medicine composition comprises *Radix salvia Miltiorrhiza* & *Radix Notoginseng* extract and *Borneol* (Bingpian) preferably in a weight ratio of (9~10):1, wherein weight of *Radix salvia Miltiorrhiza* & *Radix Notoginseng* extract is the dry weight. Said *Radix salvia Miltiorrhiza* & *Radix Notoginseng* extract is prepared from by extracting *Radix salvia Miltiorrhiza* and

*Radix Notoginseng* simultaneously. Weight ratio of crude drug of *Radix salvia Miltiorrhiza* & *Radix Notoginseng*, used as starting material, is (3~7):1, preferably (4~6):1 and most preferably 5:1. Said *Radix salvia Miltiorrhiza* & *Radix Notoginseng* extract may be prepared by conventional extraction methods, preferably the method of extracting with weak base aqueous solution. Preferably, said weak alkali aqueous solution is aqueous solution having pH value of more than or equal to 8, more preferably the pH value of 8~9, most preferably the pH value 8. For example, said *Radix salvia Miltiorrhiza* & *Radix Notoginseng* extract is prepared by a method comprising: extracting pulverized *Radix salvia Miltiorrhiza* and *Radix Notoginseng* with water or weak alkali aqueous solution, filtering, properly concentrating the filtrate, performing alcohol precipitation by adding alcohol into the concentrated solution, standing still, recovering the obtained supernatant and concentrating to give the extract.

According to the present invention, said *Radix salvia Miltiorrhiza* & *Radix Notoginseng* extract is prepared by a method comprising following steps:

a. extracting pulverized *Radix salvia Miltiorrhiza* and *Radix Notoginseng* together with water or weak alkali aqueous solution for 2~3 times, in an amount of 4~8 times the weight of the *Radix salvia Miltiorrhiza* and *Radix Notoginseng* crude drugs for each time, filtering the extract, blending the filtrate and properly concentrating the filtrate;

b. adding high concentration alcohol into the concentration solution to make a final alcohol concentration of 50~85% (v/v) and allowing to stand still to perform precipitation, filtering the supernatant, recovering alcohol from the supernatant and concentrating to give the extract.

Wherein, in step (a), said extracting temperature is kept preferably at 60~120° C. Said pH value of weak alkali aqueous solution is more than or equal to 8, preferably 8~9, most preferably 8. Said weak alkali aqueous solution is preferably sodium bicarbonate aqueous solution at a concentration of 0.3%~1% (w/w), most preferably the sodium bicarbonate aqueous solution at a concentration of 0.45% (w/w). Said filtrate is concentrated to an extract in a ratio of extract volume (L) to inputted weight of crude drug (Kg) of 1:(0.7~1.3). In step (b), alcohol is used to perform precipitation. Said final concentration of the concentrated solution is preferably at 50~80% (v/v). Said relative density of obtained extract is 1.15~1.45.

According to the present invention, said Chinese medicine composition can be prepared into any kind of pharmaceutically dosage form in accordance with conventional or frequently-used procedure, e.g. dripping pill, pill, capsule, granule, tablet, suspension, injection, syrup, tincture, powder, medicinal tea, local medicinal solution, spray, suppository, micro-capsule or other pharmaceutically acceptable dosage form, preferably the dripping pill. The dripping pill is composed of said Chinese medicine composition and matrix adjuvant.

According to the present invention, said dripping pill is composed of said Chinese medicine composition and matrix adjuvant. Preferably, the matrix adjuvant is selected from PEG-4000 or PEG-6000. Weight ratio of said Chinese medicine composition to matrix adjuvant is (0.2~0.8):1, preferably (0.29~0.7):1, more preferably (0.5~0.6):1.

According to the present invention, said dripping pill of Chinese medicine composition can be prepared by conventional methods known in prior art, also a method as follows: well mixing said Chinese medicine composition with matrix adjuvant, melting by heating, transferring the melted solution into dripping tank, letting the melted solution dripping into a low-temperature liquid paraffin, removing residual paraffin and selecting to give the final product. Wherein, melting temperature is kept at 60~100° C., preferably 75~85° C., and the liquid paraffin temperature at 0~20° C., preferably 5~15° C.

According to the present invention, said matrix adjuvant is natural dripping pill adjuvant derived from plant, which includes at least one kind of matrix adjuvant and at least one kind of plastifying adjuvant.

According to the present invention, said matrix adjuvant can be selected from the group consisting of a pharmaceutically acceptable D-ribose, fructose, xylose, fucose, raffinose, maltose, agarose, sucrose ester, D-ribonic acid-γ-lactone, erythritol, sorbitol, xylitol, arabitol, isomaltitol, lactitol, malic acid, sterin, shellac, phenylethylene glycol, polyoxyethylene alkyl ether, and the aforementioned compounds containing hydrate water.

Besides, said plastifying adjuvant is selected from the group consisting of pregelatinized starch, carboxymethyl starch, arabic gum, dextran, sesbania gum, carrageenan, Indian gum, furcellaran, tragacanth gum, tamarind gum, pectin, xanthan gum, alginic acid and the salts thereof, agar, lactose, glyceryl monostearate, polyoxyethylene monostearate, cross-linked sodium carboxylmethyl cellulose and silica.

According to the present invention, if existing or emerging synthetic matrix adjuvant and plastifying adjuvant have the same or similar quality with aforementioned natural-sourced ones, and if they have safety characteristics without toxicity, they can replace aforesaid natural plant-sourced matrix adjuvant and plastifying adjuvant as being applied in preparation of dripping pill.

According to the present invention, ratio of aforesaid matrix adjuvant to plastifying adjuvant is 1:0~1:1.5, preferably 1:0.1~1:0.9, most preferably 1:0.1~1:0.5.

According to the present invention, the method of using aforementioned matrix adjuvant and plastifying adjuvant as excipients comprises main steps:

a. selecting one or more types of aforementioned matrix adjuvant(s), or adding one or more low-melt matrix adjuvant with one or more types of aforementioned plastifying adjuvant(s), well mixing;

b. transferring obtained well-mixed matrix adjuvant or its mixture into a dripping tank, into which medicine extract is added and continued to well mixed with the adjuvant;

c. heating the obtained mixture until well being melted, dripping melted solution into cooling liquid, after being solidified, screening out the pills;

d. removing outside surface cooling liquid by wiping or a centrifuge;

e. drying the clean pills at low temperature to give the product.

In aforementioned method of preparing dripping pills, the weight ratio of said matrix adjuvant to plastifying adjuvant is 1:0~1:1.5, preferably 1:0.1~1:0.9, most preferably 1:0.1-1:0.5. The weight ratio of matrix adjuvant to active substances is 1:0.1~1:1, preferably 1:0.1~1:0.6, most preferably 1:0.2~1:0.4.

In aforementioned method of preparing dripping pills, the mixing time of active substance and matrix adjuvant is 10~30 min. The heating melting (or dripping) temperature after the active substance is well mixed with the matrix adjuvant is kept at 45~95° C., preferably 60~95° C. The cooling liquid is liquid paraffin, methyl silicon oil or vegetable oil (e.g. soybean oil or castor oil), preferably liquid paraffin or methyl silicon oil. Temperature of cooling liquid is −20~30° C., preferably 0~18° C. The inner diameter of dripper is 1.0~4.0 mm, preferably 1.2~2.5 mm. The less difference value between inner and outer diameter of dripper, the better dripping effect the pills can achieve.

According to the present invention, said dripping pill can be prepared by using cooling air instead of cooling liquid. Facility and method that are used have been recorded clearly in Chinese patent application 200710060640.1 (Title: *Method for preparing dropping pill using cool air and equipment using the method*, publication date: Oct. 8, 2008, publication No.: CN101279220A), Chinese patent application 200710060641.6 (Title: *Equipment for preparing pill using cold wind and trap cooling gas*, publication date: Jul. 30, 2008, publication No.: CN101229099A), and Chinese patent application 200710060642.0 (Title: *Equipment for preparing dropping pill with air cooled by cold trap*, publication date: Oct. 8, 2008, publication No.: CN101279221A). These documents hereby are incorporated by reference.

According to the present invention, said dripping pill can be coated by inputting material in accordance with theoretical 3 wt %~6 wt % weight increased, preferably 4 wt %. Practical coating increased weight should be no less than 80% of theoretical increased weight. According to the present invention, said dripping pill can be either coated or un-coated. In order to convenient administration, said dripping pills can be loaded into capsule.

Clinical Trial

In phase II clinical trial, a double-blind, placebo-controlled, randomized, multi-center, parallel-controlled clinical trial had been conducted to evaluate safety and efficacy of said Chinese medicine composition (coded as "T89-005-0001-AU") of present invention on patients with chronic stable angina pectoris. The objective of this phase II clinical trial was to confirm the efficacy of said Chinese medicine composition on patients with chronic stable angina pectoris, and to assess the efficacy of said Chinese medicine composition by increased exercise time in an exercise tolerance test (ETT) in accordance with the *Standard Bruce Protocol*. The second objective was to evaluate the safety and tolerance of said Chinese medicine composition on patients with chronic stable angina pectoris.

Preliminary test, after approval by the Australia Drug Administration (TGA), was conducted in Australia and New Zealand. Design of this trial was essentially the same as the trial in US (Coded as "T89-005-0003-US"), except there were only two groups in this trial: placebo group, trial group (375 mg said Chinese medicine composition prepared in accordance with EXAMPLE 11, twice a day).

This research was operated by an Australia CRO and managed by CNS. There were totally 10 patients enrolled in an Australia Center and a New Zealand Center. This trial was started in May, 2008, and finished in July, 2009. The trial of last patient was finished in May, 2009.

This trial research included two parts: the one was a 2-week study on screening the patients' baseline value in ETT into groups twice; another one was 8-week double-blind, placebo-controlled and randomized study, that is, the treadmill trial when the drug absorption reached wave peak and wave valley in $4^{th}$ week and $8^{th}$ week.

Patients who have moderate chronic stable angina pectoris, aged 18~80, and diagnosed as grade II or grade Ill angina pectoris by Canadian Cardiovascular Society (CCS) could accept the ETT in accordance with the *Standard Bruce Protocol*. Except those who had been allowed to take short-effective drugs, e.g. nitroglycerin, β-blocker or calcium channel blockers during 14-day screening stage, the patients were required to suspend drug previously used for treating angina pectoris. The patients must receive a series of inspections during the screening stage: case history, physical examination, resting electrocardiogram, measurement of blood pressure, heart rate and examination of clinical inspection items. The patients eligible for inclusion should have a detailed case history document of myocardial infarction (MI) or severe coronary heart disease, which was diagnosed by non-invasive or angiography. Moreover, their symptoms should support the diagnosis of chronic angina pectoris, and/or the angina pectoris patients had the history of motion abnormality reaction and/or ECG changes. In addition, the eligible patients should have limited sport ability (maximum TED in the *Standard Bruce Protocol* is 3~7 min), which should be confirmed on $-7^{th}$ day and $0^{th}$ day. In tolerance test, however, difference between two tests could not be more than 15% of longer test. After two visits on $-7^{th}$ day and $0^{th}$ day, the eligible patients were randomly assigned into groups.

Totally, 10 patients were included and assigned into 1 and 2 treating groups. In double-blind stage, the patients should write down the frequency of angina pectoris and dosage of short-effective nitroglycerin in daily card. According to the *Standard Bruce Protocol*, the ETT was performed on $28^{th}$ day (wave peak, 1~2 hour (s) after administration), $29^{th}$ day (wave valley, 11~13 hours after administration), $56^{th}$ day (wave peak) and $57^{th}$ day (wave valley).

According to the original plan, at least 70 patients with chronic stable angina pectoris should be enrolled, and 60 of them would complete the trial with 30 subjects in each group. However, because the researchers didn't foresee difficulties of enrolling the subjects in Australia and New Zealand, until termination of trial, there were only 10 subjects who were assigned into the groups. Among these patients, only 3 subjects didn't violate the agreement or dropped out of the research trial early, but they didn't have any statistical significance for efficacy evaluation.

Safety evaluation should be carried out on all patients who received treatment. None of severe adverse events (SAE) report about tested drug was provided in this trial, which had been recorded in the safety use document of said Chinese medicine composition.

I.1 T89-005-0003-US Clinical Trial

I.1.1 Design of Trial

Title of 89-005-0003-US is "A Phase II, Double Blind, Placebo-controlled, Randomized, Multi-Center, Parallel Group Study to Evaluate the Efficacy and Safety of T89 in Patient with Chronic Stable Angina Pectoris". The flow chart of the trial was seen in FIG. 1. In this research trial, total 125 male and female patients, aged at 18~75, were enrolled, and the trial was supervised by the iCS, a US CRO company. The enrolled patients were distributed in 15 medical centers in US. After being approved by the Institutional Review Board (IRB), the trial plan was submitted to the FDA. The first patient was enrolled in March, 2008, and the final visit of last patient on Dec. 22, 2009.

The target population of the trial was male or female patients with moderate chronic stable angina pectoris, aged 18~80, and diagnosed as grade II or grade III angina pectoris by Canadian Cardiovascular Society (CCS). The patients eligible for inclusion should have a detailed case history document of myocardial infarction (MI) or severe coronary heart disease, which was diagnosed by non-invasive or angiography. Moreover, their symptoms should support the diagnosis of chronic angina pectoris, and/or the angina pectoris patients had the history of motion abnormality reaction and/or ECG changes. Except those who had been allowed to take short-effective drugs, e.g. nitroglycerin, β-receptor blocker or calcium channel blockers during 14-day screening stage before, the patients were required to suspend drug previously used for treating angina pectoris. In addition, the eligible patients should have limited sport ability (maximum TED in the *Standard Bruce Protocol* is 3~7 min), which should be confirmed on $-7^{th}$ day and $0^{th}$ day. In tolerance test, however, difference between two tests could not be more than 15% of longer test. After two visits on $-7^{th}$ day and $0^{th}$ day, the eligible patients were randomly assigned into groups.

The participating patients were randomly assigned into 3 treating groups: placebo group, low-dose group and high-dose group (0, 125 mg or 187.5 mg, the test drug was prepared by the method of EXAMPLE 11, administrated once for 12 hours with daily dose of 0, 250 mg and 375 mg.). Other simultaneously-taken drugs for treating angina pectoris would be stopped. If need be, the short-effective nitroglycerin and a kind of β-receptor blocker or calcium channel blockers. The duration of treatment was 8 weeks.

In double-blind stage, the patients should write down the frequency of angina pectoris and dosage of short-effective nitroglycerin in daily card. According to the *Standard Bruce*

Protocol, the ETT was performed on $28^{th}$ day (wave peak, 1~2 hour (s) after administration), $29^{th}$ day (wave valley 11~13 hours after administration), $56^{th}$ day (wave peak) and $57^{th}$ day (wave valley).

I.1.2 Study Control

The whole phase II clinical trial strictly followed the requirements of the GCP. Before the drugs were distributed to study center (s), training program had been completed on the researchers, and the GCP training program and visits in the study center (s) was launched. In the trial, all of severe adverse events (SAE) report should be reviewed and approved by the Institutional Review Board (IRB). Because no SAE had taken place in relating to tested drugs and trial plan, there were no relevant suggestions proposed by the IRB during the whole trial. All publicity materials, e.g. leaflet, TV script and brochure, were not handed out, until being approved by the IRB. All patients who volunteered to take part in the test needed signing the informed consent form and achieved. The CRO clinical inspector completed monitoring all centers. Besides, the applicant and CRO had completed visiting research process and training program on related persons.

I.1.3 Determination of Sample Size

Based on the assumption of normal distribution of the ETT data and individual SD within 90 s, 30 evaluable patients were needed in each group and successful rate 80%, so as to detect the TED difference within 30 s between 187.5 mg Chinese medicine composition group and placebo group in primary endpoint. Taking 20% dropping rate into account, it was estimated to need 36 patients entering the groups.

I.1.4 Analysis of Data

All data were twice inputted into third-part provided software CRF 21 (DMsys 5.0). Under the control by the Data manager, at least two independent data inputters were needed. Before data locking, all work should be completed, including CRF review, DCF query, error checking and data cleaning. Before locking the record of data locking, the data examination committee would give a double review on the decision and reasons why the patients were excluded from ITT or PPT analysis set. Process of opening the blind was divided into steps: the first step was to, after data locking, open the grouping code and divide into three groups of A, B and C in accordance with the blind code to perform data analysis; the second step was to make clear what treating method three groups of A, B and C represented respectively.

ITT analysis set: the ITT analysis set included the patients who at least once received the ETT. Two excluded patients were present in Table 1.

TABLE 1 subjects excluded from the ITT analysis set

| No. | Reason |
|---|---|
| 101 | 1. The ETT baseline was not set up correctly on the ETT testing machine newly bought by center (s), which was found out by the clinical inspector after randomization of first patients. The ETT data results were invalid. Later on, reading function of machine was adjusted and the other patients' data had not been affected.<br>2. Difference between two baselines was more than 15%. |
| 707 | The patient was not an angina pectoris patient, and didn't have angina pectoris history. There were no symptoms of chest pain or ST-segment depression in baseline examination and ETT test. |

PPT analysis set: the PPT analysis set included the patients who received 8-week drug treatment, didn't violate the research plan, didn't take any forbidden drug and didn't have chronic obstructive pulmonary disease (COPD). The patients who missed data were permitted to stay in the set. The list of patients excluded from the PPT was seen in Table 2 and Table 3.

TABLE 2 subjects excluded from the PPT analysis set due to baseline deviation

| | Exclusion criteria | |
|---|---|---|
| No. | At least once ETT baseline more than 7 min | Difference between two baselines was more than 15% |
| 101 | | ✓ |
| 103 | ✓ | |
| 301 | ✓ | |
| 303 | | ✓ |
| 308 | | ✓ |
| 310 | | ✓ |
| 311 | | ✓ |
| 405 | | ✓ |
| 412 | | ✓ |
| 415 | | ✓ |

TABLE 3 subjects excluded due to taking forbidden accompany drugs

| No. | Forbidden drugs |
|---|---|
| 103 | metoprolol + amlodipine |
| 105 | COPD history |
| 110 | COPD history, received one-day atomizer treatment on Sep. $9^{th}$, 2009. |
| 115 | Carvedilol + amlodipine + ranolazine |
| 308 | CPOD history |
| 311 | Ranolazine |
| 412 | Metoprolol + amlodipine |
| 501 | Atenolol + nifedipine |
| 502 | No obvious symptom of COPD, but had possibility |
| 504 | Warfarin |
| 708 | Ranolazine |
| 722 | CPOD history |
| 1002 | CPOD history |
| 1103 | CPOD |
| 1107 | Warfarin |
| 1108 | Metoprolol + amlodipine |
| 1201 | Ranolazine |
| 1501 | Metoprolol + amlodipine + ranolazine |
| 1502 | Ranolazine |

Safety data set: safety data set included the patients who had taken the tested drug at least once.

Dealing with the fall-off or missing value: for patients who missed data at $57^{th}$ day, the last-observed data before was used to replace the missed value except observing the baseline. In ITT set population, 15 patients (12.2%) terminated the trial in the absence of the exercise test at $57^{th}$ day, 6 patients in Group A (43 cases), 3 patients in Group B (37 cases), and 6 patients in Group C (43 cases). The final observation time of 2 patients was at $28^{th}$ day, 4 patients at $56^{th}$ day and 2 patients at $29^{th}$ day. There were 7 patients who missed the data in the main end point at $57^{th}$ day, and had been marked with N/A because they had only baseline of the ETT.

I.1.5 Population Characteristics

About 70% of subjects were the white race; the average age was 60 years old. No obvious difference in the baseline and population characteristics between treating groups.

Figure 2:
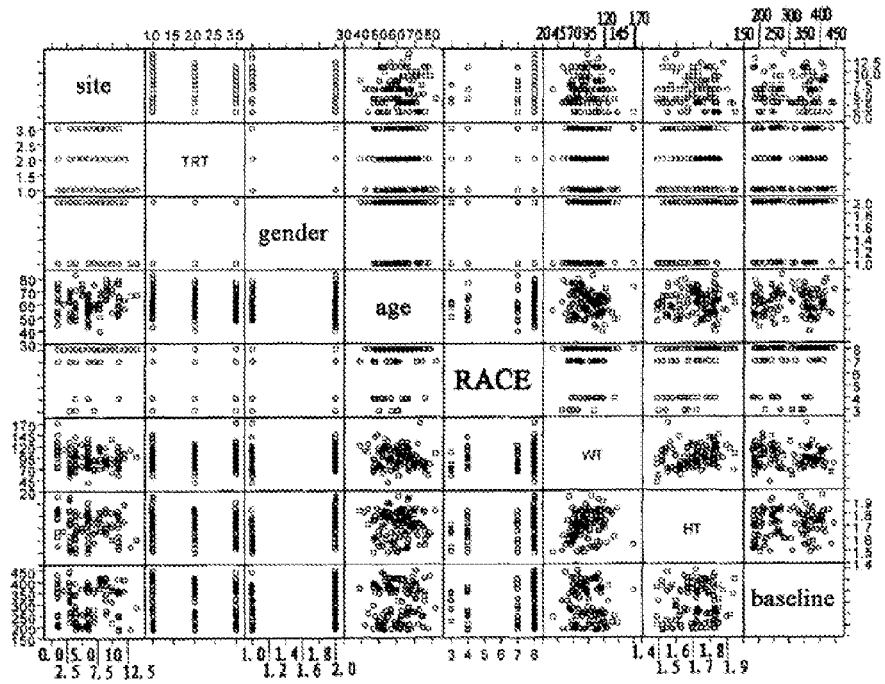
Figure 3:
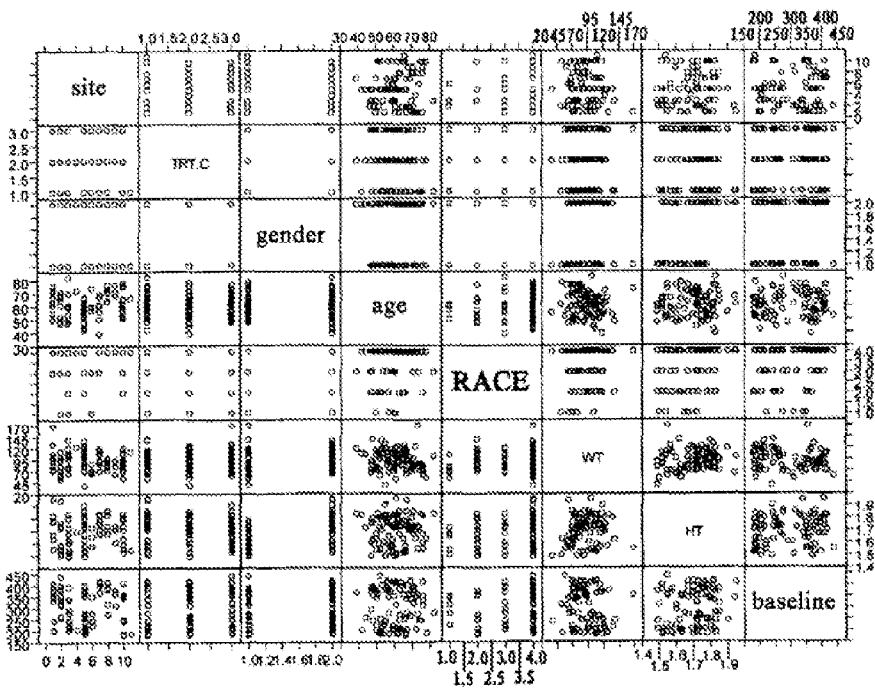

Population statistics and baseline characteristics were seen FIG. 2, FIG. 3 and Table 4.

TABLE 4 population statistical characteristics in each treating group (ITT analysis set)

| Characteristics | H (High dose) (n = 40) | L (low dose) (n = 40) | P (placebo) (n = 35) | sum (n) (n = 115) |
|---|---|---|---|---|
| Age, average (SD) (year) | 62.15 ± 9.16 | 60.68 ± 9.77 | 60.09 ± 8.64 | 61.01 ± 9.19 |
| Age, Percentage (%) | | | | |
| ≥60 | 23 (57.50) | 24 (60.00) | 18 (51.43) | 65 (56.52) |
| <60 | 17 (42.50) | 16 (40.00) | 17 (48.57) | 50 (43.48) |
| Gender, n (%) | | | | |
| Male | 33 (82.50) | 27 (67.50) | 19 (54.29) | 79 (68.70) |
| Female | 7 (17.50) | 13 (32.50) | 16 (45.71) | 36 (31.30) |
| Race, n (%) | | | | |
| White rice | 31 (77.50) | 27 (67.50) | 24 (68.57) | 82 (71.30) |
| Black rice | 2 (5.00) | 5 (12.50) | 6 (17.14) | 13 (11.30) |
| Asian | 2 (5.00) | 2 (5.00) | 1 (2.86) | 5 (4.35) |
| Other | 5 (12.50) | 6 (15.00) | 4 (11.43) | 15 (13.05) |
| Height (m), average (SD) | 1.74 ± 0.12 | 1.70 ± 0.11 | 1.69 ± 0.10 | 1.71 ± 0.11 |
| Weight (kg), average (SD) | 97.13 ± 21.82 | 90.27 ± 21.07 | 92.67 ± 23.32 | 93.39 ± 22.03 |
| TED baseline, average (SD) | 304.65 ± 87.51 | 286.35 ± 81.28 | 308.93 ± 76.84 | 299.59 ± 82.09 |

I.1.6 Efficacy Outcomes

ITT and PPT analysis set were assessed together. Without the mid-term analysis of efficacy evaluation in this trial, the P value didn't need data adjustment.

According to the *Standard Bruce Protocol*, the main indexes for therapeutic effects was to compare the change of TED when the drug content reached peak valley level in patients between treating group and placebo group in $4^{th}$ and $8^{th}$ week. The arithmetic average of mixed data collected from various centers and the standard deviation (SD) were used to evaluate therapeutic parameters. Considering the impact of comprehensive factors, e.g. the age, gender and/or body weight, food, the data calculation method on treatment difference was the arithmetic average (SD) or the analysis of least squares method (LSM), significance was 0.05.

A) Unadjusted Main Therapeutic Analysis Data

Table 5 and 6 showed summary of the main effectiveness variables of ITT and PPT analysis by the mathematics average method.

TABLE 5 summary of TED changes in ETT, $\overline{X}$ ± SD (ITT analysis set)

| Visit | Variable | H (High dose) (n = 40) | L (Low dose) (n = 40) | P (Placebo) (n = 35) |
|---|---|---|---|---|
| $-7^{th}$ day and $0^{th}$ day | TED baseline (s) | 307.25 ± 12.89 | 284.73 ± 12.31 | 312.28 ± 12.63 |
| $28^{th}$ day | TED (s) | 348.00 ± 14.58 | 310.50 ± 15.32 | 330.91 ± 17.09 |
| | Relative to the baseline, average of changes* | 43.35 ± 9.73 | 24.15 ± 8.01 | 21.99 ± 10.56 |
| | Improvement relative to the placebo group (s)** | 21.36 | 2.16 | N/A |
| $29^{th}$ day | TED (s) | 365.44 ± 16.58 | 330.38 ± 15.22 | 330.94 ± 18.90 |
| | Relative to the baseline, average of changes* | 62.21 ± 10.62 | 41.47 ± 10.06 | 22.01 ± 12.08 |
| | Improvement relative to the placebo group (s)** | 40.19*** | 19.46 | N/A |
| $56^{th}$ day | TED (s) | 368.38 ± 19.42 | 343.76 ± 16.82 | 352.85 ± 18.63 |
| | Relative to the baseline, average of changes* | 62.96 ± 12.63 | 54.48 ± 12.84 | 42.26 ± 12.17 |
| | Improvement relative to the placebo group (s)** | 20.69 | 12.2 | N/A |
| $57^{th}$ day | TED (s) | 370.76 ± 18.36 | 341.33 ± 15.25 | 352.66 ± 19.18 |
| | Relative to the baseline, average of changes* | 65.55 ± 14.66 | 54.98 ± 11.94 | 43.73 ± 13.26 |
| | Improvement relative to the placebo group (s)** | 21.82 | 11.25 | N/A |

*In first step, the average changing value of TED compared with the baseline was calculated by calculating the change of TED between each individual and baseline; in the second step, the average value and SD of that day in the group was calculated.

**The improvement data relative to the placebo group was calculated by subtracting the average value of placebo group from the corresponding index of treating group in the same day.

***$P < 0.05$, statistical significance

In the ITT analysis set, there were 4 subjects who terminated the trial without performing exercise test in $8^{th}$ week valley concentration, 12 subjects (27.9%) in high dose group (187.5 mg, b.i.d.), 9 subjects (20.9%) in low dose group (125 mg, b.i.d.) and 4 subjects (10.8%) in placebo group.

B) Main Effective Data Analysis, Adjusted in Accordance with the Age

Change of TED did not have a positive correlation with baseline, body weight and gender (FIG. 8a and FIG. 8b). It was observed that change of TED had a positive correlation with the age in all visits of ETT in ITT analysis set (FIG. 9).

TABLE 6 summary of TED change compared with the ETT, $\overline{X} \pm SD$ (PPT analysis set)

| Visit | Variable | H (High dose) (n = 26) | L (Low dose) (n = 32) | C (placebo) (n = 31) |
|---|---|---|---|---|
| $-7^{th}$ day and $0^{th}$ day | Baseline TED (s) | 295.46 ± 17.29 | 292.59 ± 14.56 | 311.80 ± 14.28 |
| $28^{th}$ day | TED (s) | 346.88 ± 19.66 | 314.28 ± 15.44 | 332.71 ± 18.83 |
| | Relative to the baseline, average of changes* | 51.42 ± 12.68 | 21.69 ± 6.19 | 20.90 ± 11.33 |
| | Improvement relative to the placebo group (s)** | 30.52 | 0.78 | N/A |
| $29^{th}$ day | TED (s) | 360.00 ± 21.81 | 329.41 ± 16.46 | 335.00 ± 20.10 |
| | Relative to the baseline, average of changes* | 64.54 ± 14.08 | 40.32 ± 10.06 | 23.19 ± 12.18 |
| | Improvement relative to the placebo group (s)** | 41.34*** | 17.13 | N/A |
| $56^{th}$ day | TED (s) | 360.48 ± 26.46 | 343.03 ± 17.91 | 353.29 ± 20.29 |
| | Relative to the baseline, average of changes* | 62.90 ± 16.45 | 56.47 ± 14.06 | 48.53 ± 11.31 |
| | Improvement relative to the placebo group (s)** | 14.37 | 7.93 | N/A |
| $57^{th}$ day | TED (s) | 375.08 ± 26.70 | 343.56 ± 16.33 | 359.55 ± 20.16 |
| | Relative to the baseline, average of changes* | 79.62 ± 20.96 | 50.97 ± 13.22 | 47.74 ± 13.63 |
| | Improvement relative to the placebo group (s)** | 31.87 | 3.23 | N/A |

Figure 4:
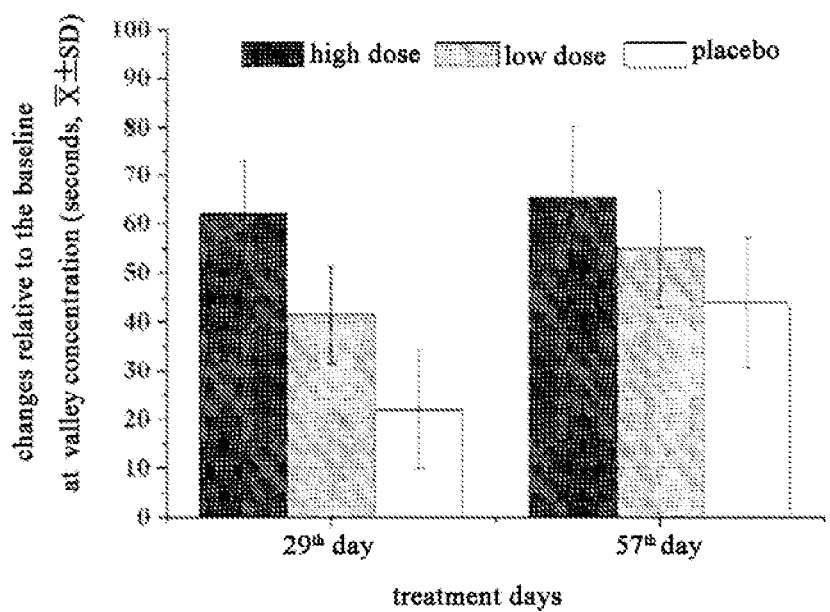
Figure 5:
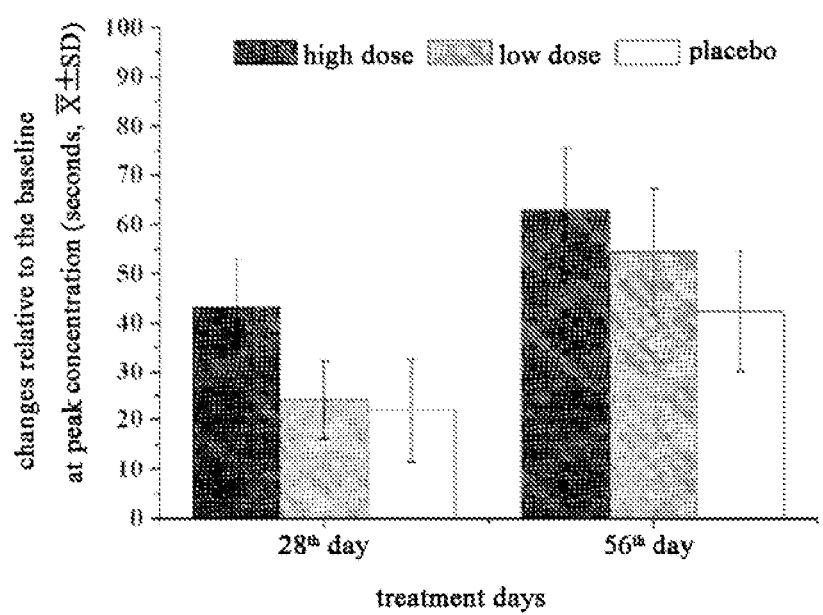

*In first step, the average changing value of TED compared with the baseline was calculated by calculating the change of TED between each individual and baseline; in the second step, the average value and SD of that day in the group was calculated.
**The improvement data relative to the placebo group was calculated by subtracting the average value of placebo group from the corresponding index of treating group in the same day.
***P < 0.05, statistical significance As shown in table 5, FIG. 4 and FIG. 5, for the population eligible to ITT analysis set, the change of TED average value was more than the one in placebo group in patients who had taken the Chinese medicine composition (187.5 mg or 125 mg, t.i.d.). The improvement result of patients in high dose group (187.5 mg, b.i.d.) taking the Chinese medicine composition was much higher than that in low dose group (125 mg, b.i.d.) at peak and valley concentration, in support of dose-effect relationship. Similar results taken place in PPT analysis set, please table 6, FIG. 6 and FIG. 7. It was illustrated the effect of the Chinese medicine composition on anti-angina pectoris.

Considering the correlation between the age and TED improvement, and influence of age, linear mixed model (LMM) was used to calculate the statistically significant difference between treatment group and placebo group by the LSM. (Table 7, 8 and FIG. 10a-b. FIG. 10a-b showed the analysis of LSM on the improvement of TED relative to the baseline in the ITT analysis set population separately at peak and valley concentration; FIG. 10a showed the analysis of LSM on the improvement of TED relative to the baseline in the ITT analysis set population at valley concentration; FIG. 10b showed the analysis of LSM on the improvement of TED relative to the baseline in the ITT analysis set population at peak concentration.)

TABLE 7 analysis of LSM on the improvement of TED in ETT, $\overline{X} \pm SD$ (ITT analysis set)

| | TED change | B (High dose) (n = 40) | A (Low dose) (n = 40) | C (Placebo) (n = 35) |
|---|---|---|---|---|
| $28^{th}$ day | Change percentage of TED relative to the baseline by LSM | 45.40 (8.90) | 23.55 (8.88) | 20.33 (9.50) |
| | Improvement vs. placebo (p-value) | 25.07 (p = 0.057) | 3.22 (p = 0.80) | — |
| $29^{th}$ day | Change percentage of TED relative to the baseline by LSM | 63.74 (10.55) | 41.31 (10.53) | 20.49 (11.14) |
| | Improvement vs. placebo (p-value) | 43.25* (p = 0.005) | 20.81 (p = 0.18) | — |
| $57^{th}$ day | Change percentage of TED relative to the baseline by LSM | 65.02 (11.84) | 54.88 (11.82) | 39.59 (12.36) |
| | Improvement vs. placebo (p-value) | 25.42 (p = 0.14) | 15.28 (p = 0.37) | — |
| $56^{th}$ day (LOCF) | Change percentage of TED relative to the baseline by LSM | 67.03 (12.77) | 54.70 (12.91) | 42.31 (13.81) |
| | Improvement vs. placebo (p-value) | 24.71 (p = 0.19) | 12.38 (p = 0.51) | — |

P < 0.05, statistically significant difference

TABLE 8 analysis of LSM on the improvement of TED in ETT, $\bar{X} \pm SD$ (ITT analysis set)

| | TED change | H (High dose) (n = 26) | L (Low dose) (n = 32) | P (placebo) (n = 31) |
|---|---|---|---|---|
| 28th day | Change percentage of TED relative to the baseline by LSM | 53.60 (10.60) | 21.36 (9.52) | 19.42 (9.69) |
| | Improvement vs. placebo (p-value) | 34.18* (p = 0.02) | 1.94 (p = 0.89) | — |
| | Change percentage of TED relative to the baseline by LSM | 21.13 (4.12) | 8.10 (3.70) | 6.53 (3.77) |
| | Improvement vs. placebo (p-value) | 14.60* (p = 0.01) | 1.57 (p = 0.77) | — |
| 29th day | Change percentage of TED relative to the baseline by LSM | 66.35 (12.67) | 40.40 (11.56) | 21.60 (11.60) |
| | Improvement vs. placebo (p-value) | 44.74* (p = 0.01) | 18.79 (p = 0.25) | — |
| | Change percentage of TED relative to the baseline by LSM | 24.87 (5.35) | 15.59 (4.89) | 6.85 (4.90) |
| | Improvement vs. placebo (p-value) | 18.01* (p = 0.015) | 8.73 (p = 0.21) | — |
| 56th day | Change percentage of TED relative to the baseline by LSM | 65.56 (14.50) | 56.35 (13.19) | 46.43 (13.22) |
| | Improvement vs. placebo (p-value) | 19.13 (p = 0.33) | 9.91 (p = 0.60) | — |
| | Change percentage of TED relative to the baseline by LSM | 22.64 (5.81) | 23.47 (5.28) | 15.07 (5.30) |
| | Improvement vs. placebo (p-value) | 7.57 (p = 0.34) | 8.40 (p = 0.26) | — |
| 57th day (LOCF) | Change percentage of TED relative to the baseline by LSM | 82.94 (16.48) | 50.47 (14.80) | 45.47 (15.07) |
| | Improvement vs. placebo (p-value) | 37.47 (p = 0.10) | 5.00 (p = 0.81) | — |
| | Change percentage of TED relative to the baseline by LSM | 30.87 (6.57) | 20.93 (5.90) | 15.68 (6.00) |
| | Improvement vs. placebo (p-value) | 15.19 (p = 0.09) | 5.24 (p = 0.53) | — |

As shown above, there was an obvious dose-effect relationship in TED improvement. That is to say, as the dose increased, the efficacy became more significant. For example, on 29th day, compared with the placebo group, the high dose group and low dose group were increased by 19 s and 45 s respectively.

On 28th and 29th day, there was a statistically significant difference between high dose group and placebo group.

C) Secondary Effective Data Analysis

The secondary effective data included the weekly frequency of angina (WFA), the weekly nitroglycerin consumption (WNC), the time to ST depression (TSTD), the time to chest pain (TCP) and the quality of life (QoL). ECG and biochemical indices were monitored as exploratory parameters.

Figure 12:
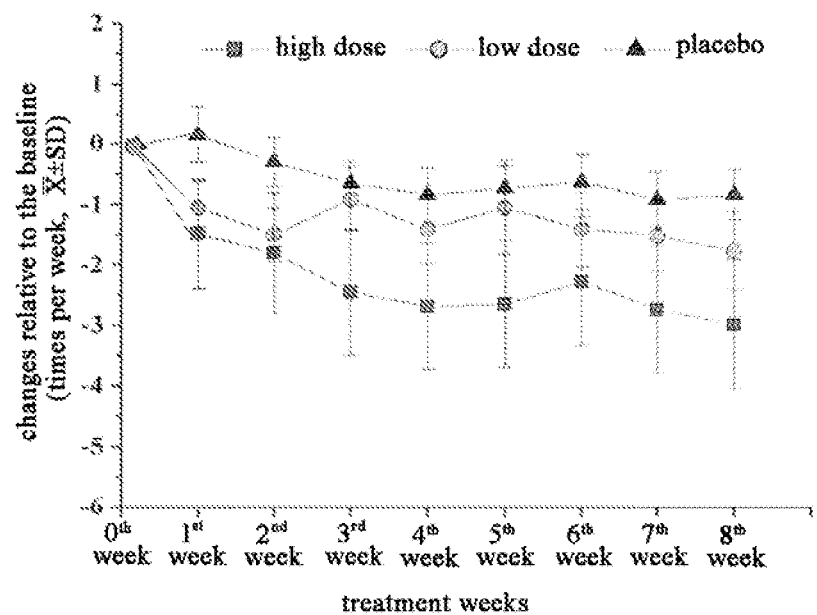
Figure 12:
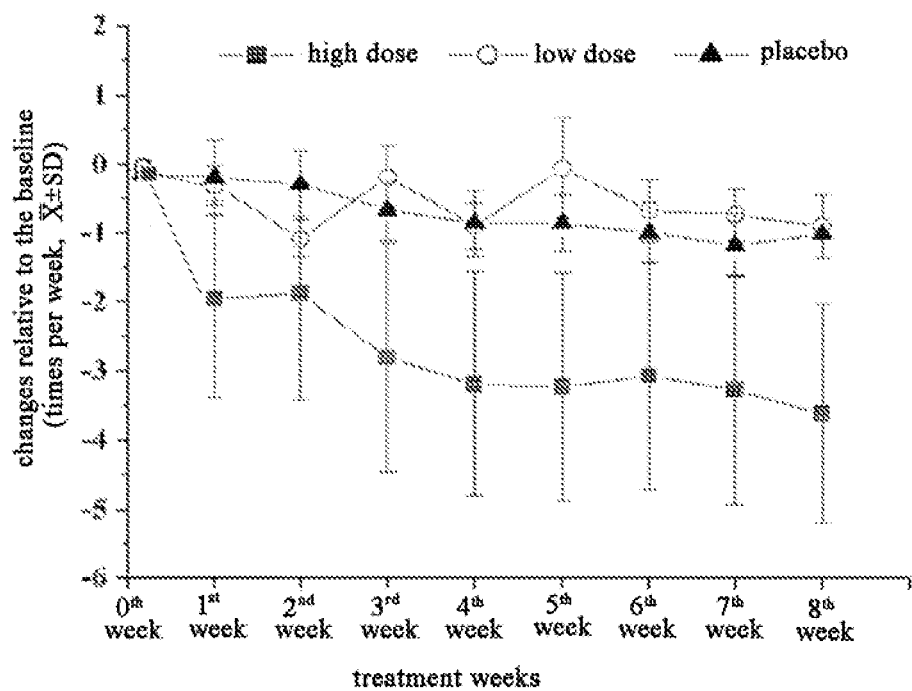
Figure 13:
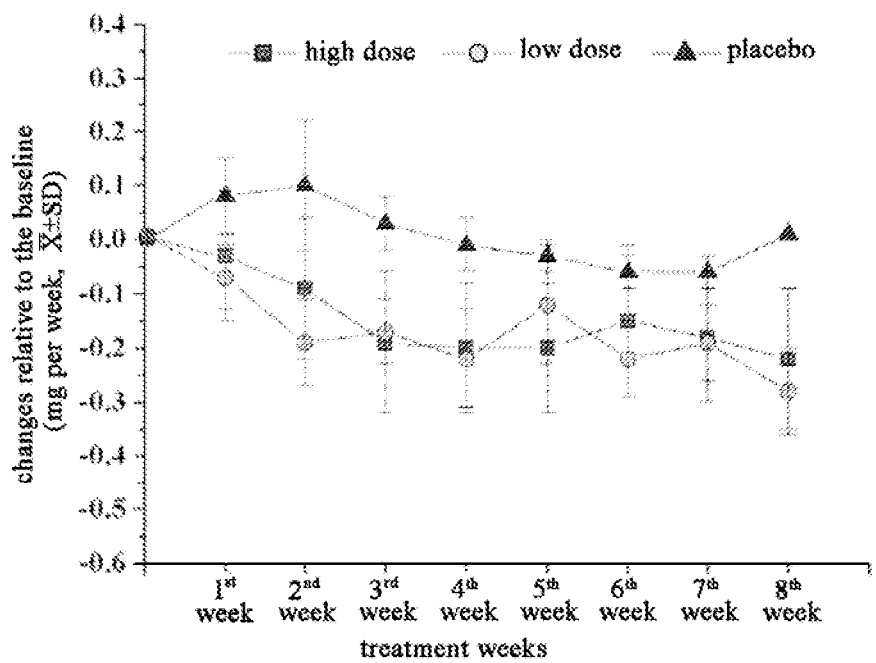
Figure 13:
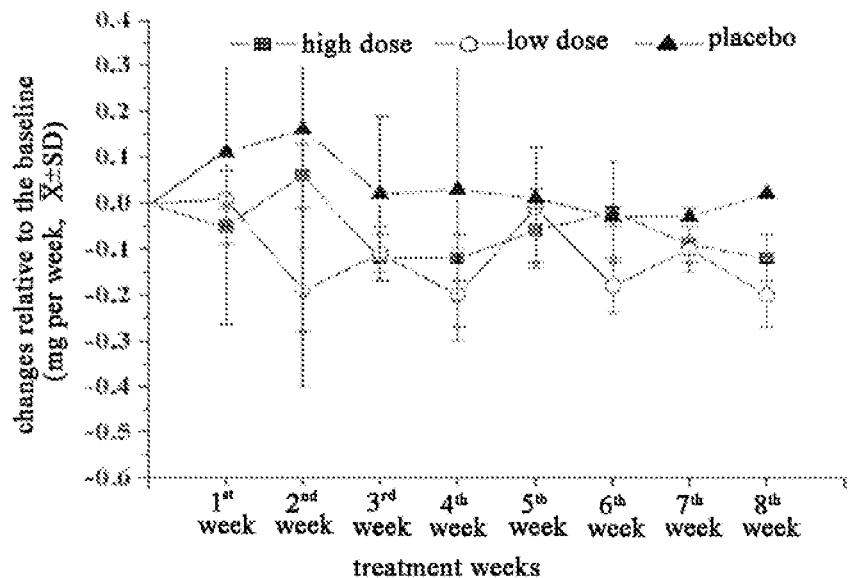

As shown in FIG. 12a and FIG. 12b, compared with the placebo group and low dose group (125 mg, b.i.d.), there was a clinical significance in decreasing average frequency of angina pectoris in high dose group (187.5 mg, b.i.d). Compared with the placebo group, FIG. 13a and FIG. 13b showed that two treatment groups (187.5 mg and 125 mg) had a significant efficacy in clinically decreasing the dose. The WFA of average baseline was 2.74 times per week, the WNC of average baseline 0.53 mg per week.

In the PPT set, compared with the placebo group, the frequency of angina pectoris and nitroglycerine consumption decreased significantly in patients who had taken the Chinese medicine composition. In the IIT set, there were 20 patients who had taken the forbidden drug, and it was likely to reduce the clinical effects of the Chinese medicine composition. FIG. 11a-b showed the analysis of LSM on the improvement of TED relative to the baseline in the PPT analysis set population separately at peak and valley concentration. FIG. 11a showed the analysis of LSM on the improvement of TED relative to the baseline in the PPT analysis set population at valley concentration; FIG. 11b showed the analysis of LSM on the improvement of TED relative to the baseline in the PPT analysis set population at peak concentration.

Figure 14:
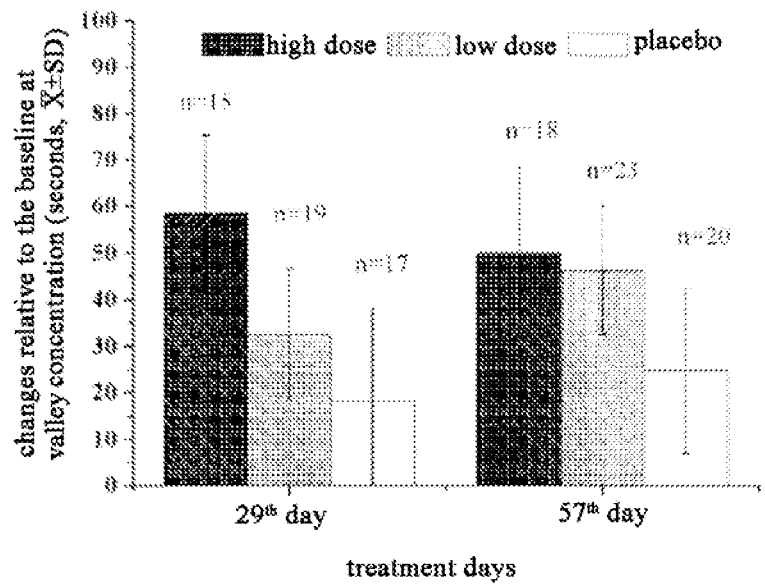

As shown in table 9 and FIG. 14, compared with the placebo group, the TCP (peak value and valley value) was significantly increased in relative to the baseline in both treatment groups of Chinese medicine composition. It was illustrated that the Chinese medicine composition had the antianginal effect.

TABLE 9 change of the attack time of angina pectoris (s) in the ETT, $\bar{X} \pm SD$ (ITT analysis set)

| Treating time | H (High dose) | L (Low dose) | P (Placebo) |
|---|---|---|---|
| 0th day | 280.18 ± 16.33 (n = 25) | 274.41 ± 14.43 (n = 23) | 293.50 ± 16.78 (n = 26) |
| 28th day | 333.88 ± 21.90 (n = 17) | 309.00 ± 21.56 (n = 18) | 308.28 ± 25.12 (n = 18) |
| 29th day | 329.06 ± 25.34 (n = 15) | 311.95 ± 21.19 (n = 19) | 300.59 ± 27.31 (n = 17) |
| 56th day | 338.56 ± 28.69 (n = 16) | 332.35 ± 22.04 (n = 17) | 327.60 ± 26.22 (n = 15) |
| 57th day | 337.78 ± 24.51 (n = 18) | 336.26 ± 19.19 (n = 23) | 318.60 ± 26.12 (n = 20) |

Figure 15:
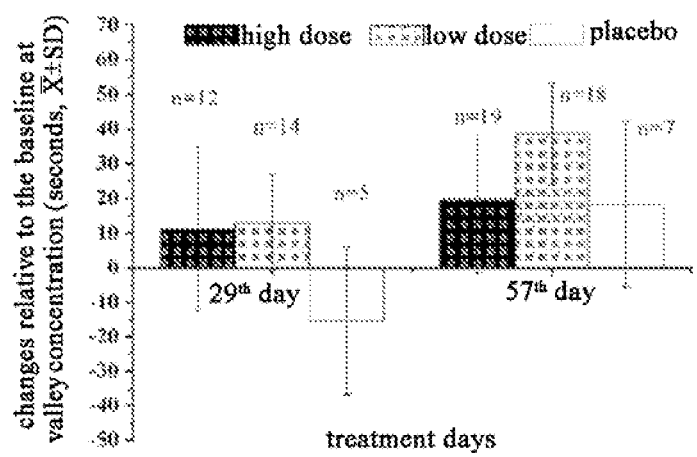

As shown in table 10 and FIG. 15, there was comparability in the change of TSTD between the high dose group (wave valley) and low dose group. Compared with the placebo group, there was a statistically significant difference in both treatment groups. It was illustrated that the Chinese medicine composition had the anti-myocardial ischemia effect. Although analysis of the ST-segment depression under relative low n value might decrease the reliability of the result, this trend was consistent with the results of main endpoint.

TABLE 10 time of 0.1 mv ST-segment depression in the ETT(s), $\overline{X} \pm SD$ (ITT analysis set)

| Treating time | H (High dose) (n = 40) | L (Low dose) (n = 40) | P (Placebo) (n = 35) |
|---|---|---|---|
| $0^{th}$ day | 295.18 ± 19.34 (n = 20) | 261.29 ± 19.77 (n = 21) | 288.81 ± 21.23 (n = 19) |
| $28^{th}$ day | 309.00 ± 39.08 (n = 12) | 300.15 ± 24.53 (n = 13) | 298.40 ± 68.86 (n = 5) |
| $29^{th}$ day | 308.25 ± 41.81 (n = 12) | 292.93 ± 26.61 (n = 14) | 277.80 ± 59.95 (n = 5) |
| $56^{th}$ day | 321.80 ± 40.96 (n = 10) | 308.82 ± 28.87 (n = 11) | 274.50 ± 61.38 (n = 4) |
| $57^{th}$ day | 321.79 ± 31.73 (n = 19) | 287.00 ± 27.65 (n = 18) | 306.57 ± 34.99 (n = 7) |

D) Analysis of Biochemical Indices and Life Quality Questionnaire

Figure 16:
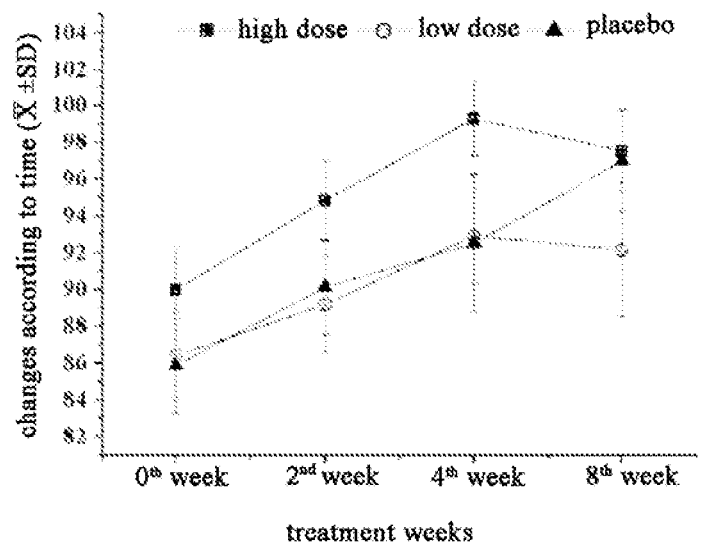

The Seattle Angina Questionnaire (SAQ) was used to investigate the improvement of life quality. No statistically significant difference had been found between treatment groups and placebo group (FIG. 16).

In this trial, the biochemical markers were analyzed only for exploring useful biochemical indices for clinical trial or clinical monitoring in the future. The statistical difference between treatment groups had not been assessed. An exploratory model analysis was done on biochemical indices, the main endpoint index and secondary endpoint index. In addition, the change of biochemical indices between different times, different dose groups and different subgroups was monitored.

The average of aforementioned biochemical indices was present as follows, which provided us with some enlightenment significance.

Figure 17:
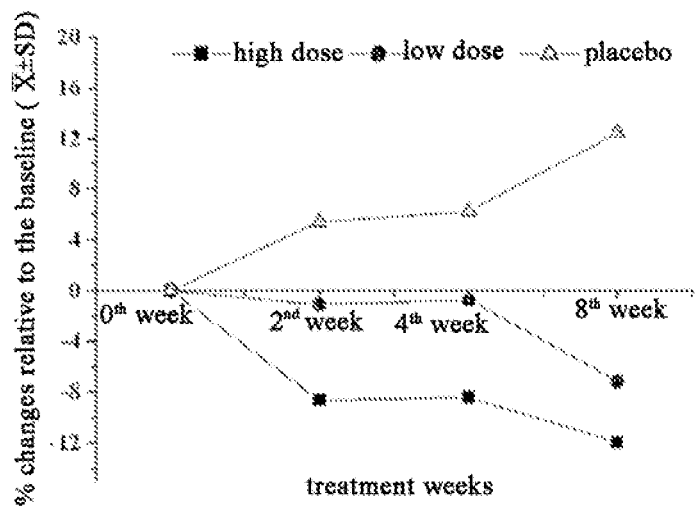
Figure 18:
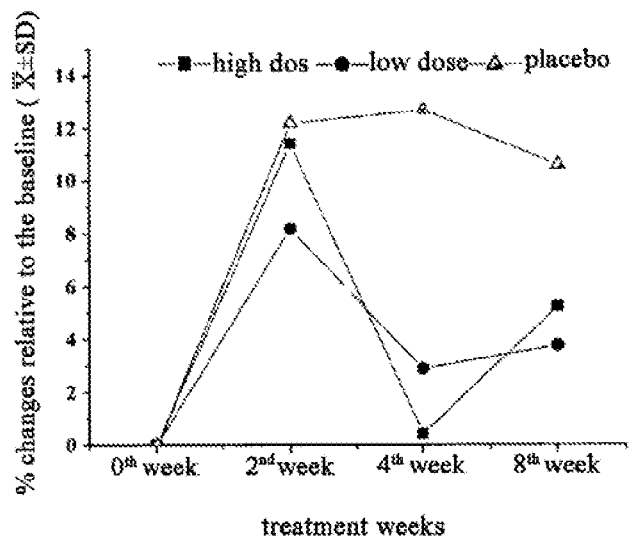

As shown in FIG. 17, compared with the placebo group, BNP of both treatment groups was decreased obviously since the first visit. On $14^{th}$ day, compared with the placebo group, LP-PLA2 value of both treatment groups was lowered slightly. Later on $28^{th}$ day, LP-PLA2 value of patients who taken the Chinese medicine composition in both treatment groups was decreased greatly. (FIG. 18)

Figure 19:
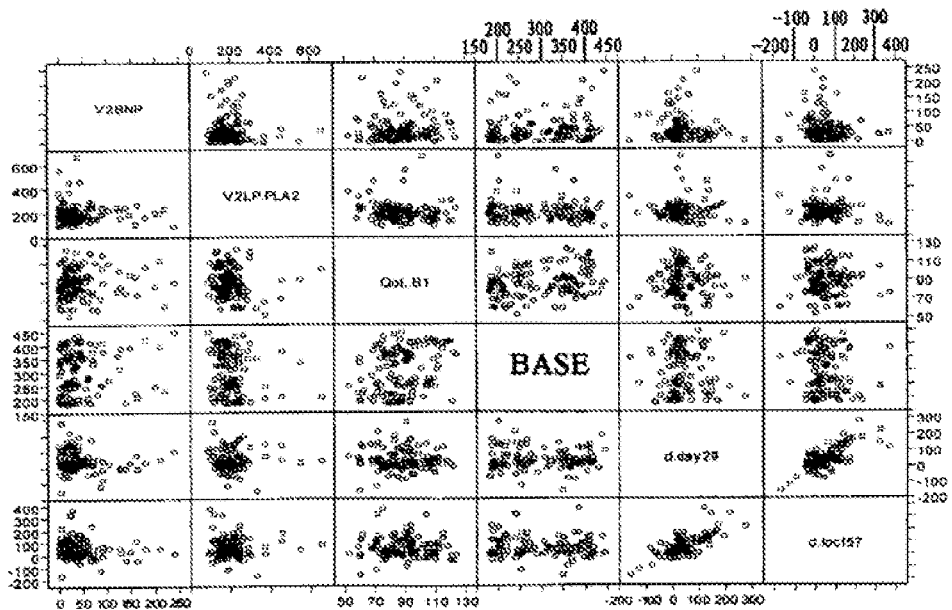

However, aforementioned biochemical indices had no relationship not only with each other, but also with the baseline value of TED and the change of TED on $29^{th}$ day and $57^{th}$ day. It was unable to establish a relevance or predictive model. Accordingly, efficacy evaluation by biochemical indices was yet to be confirmed. FIG. 19 showed the correlation between the biochemical indices and the ETT.

I.1.7 Grouping Trial

In order to evaluate whether the effectiveness of the Chinese medicine was kept consistent with a wide range of chronic angina pectoris population, an exploratory analysis had been done on different groups. Age (<64.5 years old or 64.5 years old) and TED baseline (<300 s or ≥300 s) were respectively regarded as the inclusion criteria for each group.

Figure 20:
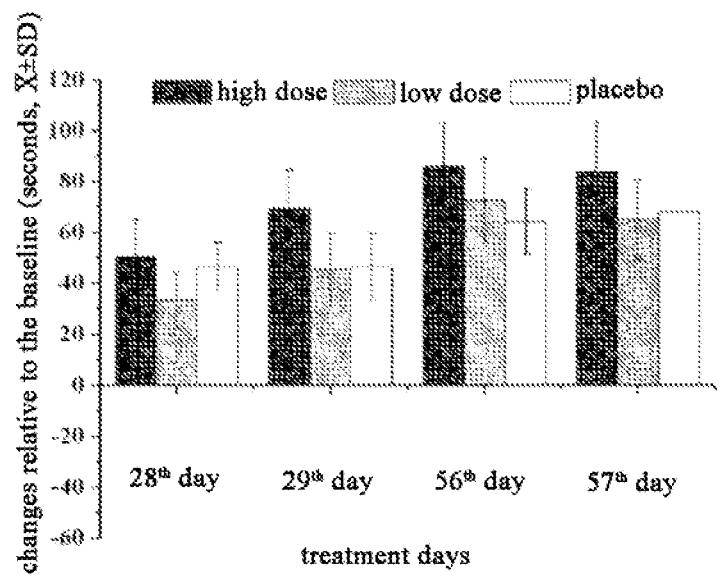
Figure 20:
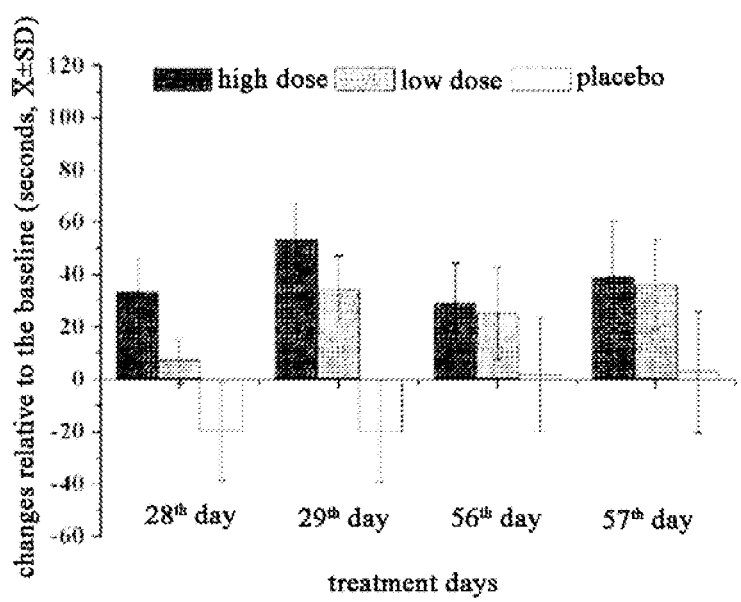

Compared with the group (younger than 64.5 years old), TED was apparently improved in older patients who were treated with different dose of the Chinese medicine composition. It was noteworthy that the placebo produced much more effect in <64.5 years age group (FIG. 20a) than 64.5 years age group (FIG. 20b). FIG. 20a-b depicted the change of TED relative to the baseline in populations with different ages. FIG. 20a depicted the change of TED relative to the baseline in populations (<64.5 years old). FIG. 20b depicted the change of TED relative to the baseline in populations (64.5 years old). The patients in 64.5 years age group, however, were treated by the placebo with a little or no effect, or even lower than the baseline. This phenomenon could explain why the older population had a worse health than that of the younger. Accordingly, their health could hardly be improved only by the placebo. These results suggested that in this study the elderly population might be more sensitive to the efficacy of the Chinese medicine composition in primary endpoint.

Figure 21:
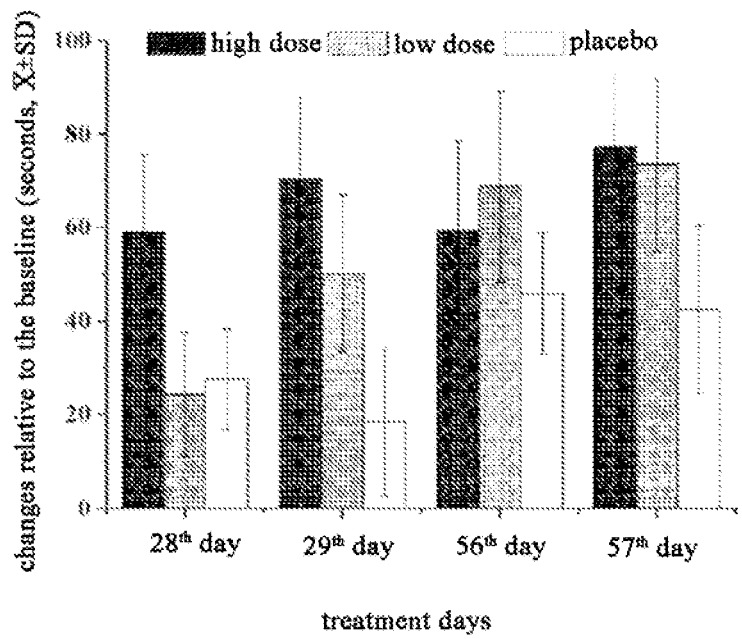
Figure 21:
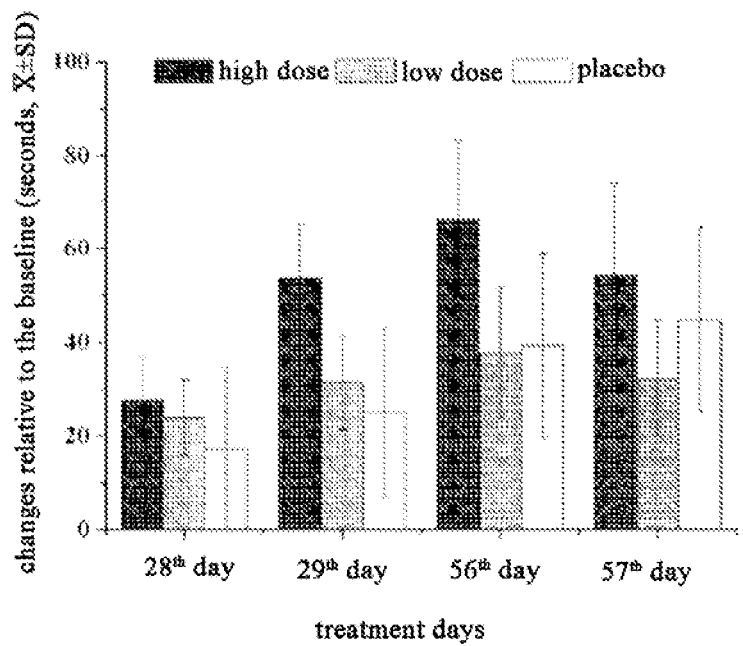

Similarly, the placebo produced a clearer effect in relatively better health group (according to baseline TED value, baseline 300 s) than that in <300 s group. These results were same with the conclusion drawn from the age grouping (FIG. 21a). The poorer health the patients had in baseline level, the less improvement effect that was produced by the placebo (FIG. 21b).

I.1.8 Evaluation of Treatment Compliance

Figure 22:
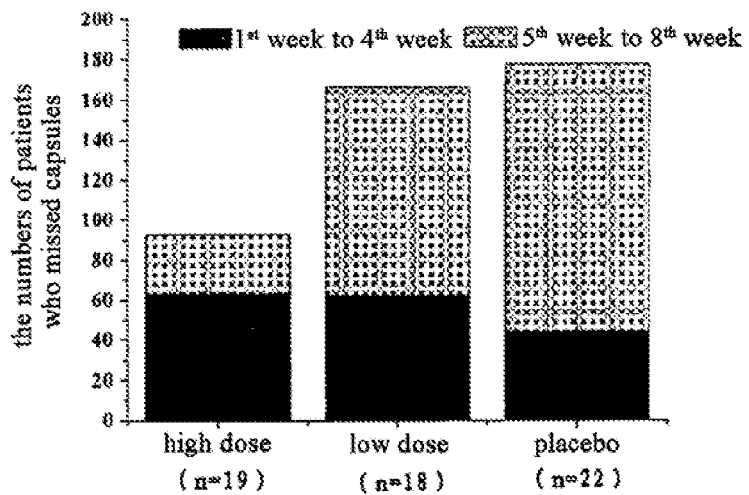

As shown in the evaluation of drug compliance, the number of patients who missed taking at least one capsule was distributed evenly among three treatment groups (FIG. 22). FIG. 22 illustrated the number of patients who missed taking the capsule at treatment groups of different doses in the ITT analysis set. The poorest compliance was the placebo group. There were 48%, 45% and 63% of patients who missed taking at least one capsule respectively among high dose treatment group, low dose treatment group and placebo group.

As being suggested in these results, the patients in the placebo group had no incentive to continue to take the drug when they found no improvement after being treated with the drug. By contrast, the patients in the high dose group maybe had a stronger motivation to take the drug seriously in part because they got a satisfactory efficacy during treatment. When the patients in the placebo group found no effect after 4-week "tryout", they quitted taking most of the drugs at the end of secondary treatment period. However, the patients in high dose group missed fewer dose, when they got benefits from the treatment. Further, this supported our conclusion.

I.1.9 Efficacy Summary

As shown in the phase II clinical trial (T89-005-003-US), administration of drug (b.i.d.) could therapeutically improve the main endpoint indices (total time of ETT at valley content of the end of $4^{th}$ week and $8^{th}$ week). Compared with the placebo group, improving the ETT by the Chinese medicine composition (187.5 mg) was of statistical and clinical significance on $29^{th}$ day and $57^{th}$ day (valley value).

Tolerance time in the ETT showed a clear dose-effect relationship. After 4-week treatment, compared with the baseline value (300s), the tolerance time of both low dose and high dose groups were increased respectively by 17 s and 44 s (valley value). With the improved training effect after 8-week treatment in the placebo group, the change of both high dose and low dose groups was 28 s, compared with the placebo group. Absolute value of the TED started to rise continuously from $28^{th}$ day and $29^{th}$ day.

The TED change of the valley level in each dose group was more than that of the peak level on $4^{th}$ week and $8^{th}$ week, which illustrated a time delay between the maximum effect of the Chinese medicine composition and concentration. Due to having a different mechanism with the nitroglycerin in antianginal effect, this time delay happening to the Chinese medicine composition was understandable. There was no data in support of the training effect possibility (the valley ETT was performed at second day after the peak ETT). Both peak and valley TED were same in the placebo.

Aforementioned results analyzed not only by the ITT set, but also the PPT set, were consistent. More importantly, other secondary efficacy indices consistently pointed to a unified trend, e.g. life quality improvement, delayed attack of angina pectoris in the ETT, delayed ST-segment depression, lowered weekly frequency of angina pectoris, reduced weekly nitroglycerin consumption and biochemical indices. Almost, they followed the same dose-effect relationship and were of same clinical and statistical significance. In any case, once the analysis results were of statistical significance, the sample size was proven to be reasonable. Accordingly, although aforesaid results were obtained on the basis of the sample size of about 30 patients in each treatment group, any random possibility of what efficacy we had observed in clinic was excluded by the strong combination of evidence and statistical significance.

Aforementioned results were consistent with the analysis in the ITT set and PPT set. The difference between the treatment group and the placebo group was usually larger whether in main endpoint or secondary endpoint, whether at $4^{th}$ week or $8^{th}$ week.

I.1.1.0 Safety Results

The method of "Safety Dataset" (SD) was used for the safety analysis, including all the patients who received at least once drug treatment. The 123 subjects were included in the SD. The patients' information and drugs they used were listed in table 11. Number of adverse drug reaction (ADR) and its occurrence at different stages were investigated. The patients who stopped taking drugs in advance because of the severe adverse events (SAE) and/or the adverse event (AE) had been listed in following table.

TABLE 11 administration of drugs in different groups (SD)

| Information | | Low dose group | High dose group | Placebo group |
|---|---|---|---|---|
| Serial number of patients | | 42 | 44 | 38 |
| Male (case) | | 28 | 37 | 21 |
| Female (case) | | 13 | 7 | 17 |
| Average age (year) | | 60.5 | 61.7 | 61.0 |
| Administration of drug (case) | Day 1-14 | 1 | 1 | 0 |
| | Day 15-28 | 2 | 4 | 1 |
| | >Day 28 | 38 | 39 | 37 |
| Average dosing period | | 53.9 | 52.8 | 55.3 | a) Summary of Safety Data

By analysis, in total 123 patients, there were 51% of subjects having the ADR (21/41) in the low dose group, 61% in the high dose group (27/44), and 66% in the placebo group (25/38). Most of the ADR was light in the clinical trial, and had no relationship with the tested drug. All ADRs were listed in table 12. Among them, the CHD symptoms (e.g. tachypnea, chest tightness and chest pain), the pain symptoms (e.g. neck, shoulder, back were muscular, leg, arm, hand and tooth pain) and flu symptom (e.g. fever, snivel, sinus congestion and cough) should not be regarded as the ADR, but can be used as a reference. In addition, there were some ADRs that occurred before drug treatment. If these ADRs were eliminated from the AE table, the number of AE patients might be reduced significantly.

Compared with the placebo group, none of obvious evidence was present to support the prolonged QTc (QT interval corrected value) on $14^{th}$ day, $4^{th}$ week and $8^{th}$ week. 5 SAEs were unrelated with the study or drug. Other AEs were few and relative small, which occurred before the clinical trial. Maybe, they were unrelated with the drugs (e.g. tooth pain, flu or chest pain). By cross-comparison, there was a same incidence rate in the placebo group.

TABLE 12

Adverse drug reaction rate in each group (SD)

| | Adverse drug reaction | | Low dose event | High dose Event | Placebo group event |
|---|---|---|---|---|---|
| System | Fatigue | | 3 (7.3%) | 4 (9.1%) | 5 (13.2%) |
| | Pain (neck, shoulder, back, muscle, leg, arm, hand, tooth) | | 5 (12.2%) | 3 (6.8%) | 5 (13.2%) |
| | Flu (fever, snivel, sinus, cough) | | 4 (9.8%) | 4 (9.1%) | 0 (0%) |
| | Allergy | | 1 (2.4%) | 2 (4.5%) | 0 (0%) |
| | Systemic infection | | 0 (%) | 1 (2.3%, bacterial infection) | 1 (2.6%, Local infection) |
| | Congestion | | 0 (0%) | 0 (0%) | 1 (2.6%) |
| | Cramp (body and limb) | | 1 (2.4%) | 0 (0%) | 0 (0%) |
| | Weight gain | | 0 (0%) | 0 (0%) | 1 (2.6%) |
| | Swelling | Hand | 1 (2.4%) | 0 (0%) | 1 (2.6%) |
| | | Arm | 1 (2.4%) | 0 (0%) | 0 (0%) |
| | | Toe | 1 (2.4%) | 0 (0%) | 0 (0%) |
| | | Foot | 0 (0%) | 1 (2.3%) | 0 (0%) |
| | Numbness | Paralysis | 0 (0%) | 1 (2.3%) | 0 (0%) |
| | | Toe | 1 (2.4%) | 0 (0%) | 0 (0%) |
| | | Hand | 1 (2.4%) | 1 (2.3%) | 0 (0%) |
| | | Arm | 0 (0%) | 2 (4.5%) | 0 (0%) |
| Heart system | Short breath, chest pain, chest tightness, chest pain/uncomfortableness* | | 5 (12.2%) | 4 (9.1%) | 9 (23.7%) |
| | Coronary atherosclerotic heart disease (CAHD) | | 0 (0%) | 1 (2.3%) | 0 (0%) |
| | Atrial fibrillation | | 0 (0%) | 1 (2.3%) | 1 (2.6%) |
| | Acute myocardial infarction | | 1 (2.4%) | 0 (0%) | 0 (0%) |
| | CAD deterioration | | 0 (0%) | 0 (0%) | 1 (2.6%) |
| | Atrial flutter | | 0 (0%) | 1 (2.3%) | 0 (0%) |
| | Abnormal heart beating | | 0 (0%) | 2 (4.5%) | 1 (2.6%) |
| | Vascular lesion | | 0 (0%) | 0 (0%) | 1 (2.6%) |

TABLE 12-continued

Adverse drug reaction rate in each group (SD)

| | Adverse drug reaction | Low dose event | High dose Event | Placebo group event |
|---|---|---|---|---|
| Digestive system | Dyspepsia | 1 (2.4%) | 1 (2.3%) | 3 (7.9%) |
| | Nausea | 2 (4.9%) | 1 (2.3%) | 0 (0%) |
| | Vomit | 2 (4.9%) | 1 (2.3%) | 0 (0%) |
| | Gastric emphysema | 1 (2.4%) | 2 (4.5%) | 0 (0%) |
| | Defecation | 1 (2.4%) | 0 (0%) | 0 (0%) |
| | Diarrhea | 1 (2.4%) | 0 (0%) | 2 (5.3%) |
| | Stomach burn | 0 (0%) | 4 (9.1%) | 0 (0%) |
| | Gastrointestinal discomfort | 0 (0%) | 0 (0%) | 2 (5.3%) |
| | Gastric discomfort | 0 (0%) | 1 (2.3%) | 1 (2.6%) |
| | Oral abnormal flavor | 0 (0%) | 1 (2.3%) | 0 (0%) |
| | Mouth bubble | 0 (0%) | 0 (0%) | 1 (2.6%) |
| | Defecate | 0 (0%) | 1 (2.3%) | 0 (0%) |
| | Diverticulitis | 1 (2.4%) | 1 (2.3%) | 0 (0%) |
| | Gastroenteritis | 0 (0%) | 1 (2.3%) | 0 (0%) |
| Respiratory system | Tonsillitis | 3 (7.3%) | 0 (0%) | 0 (0%) |
| | Upper respiratory tract | 1 (2.4%) | 1 (2.3%) | 1 (2.6%) |
| | Bronchitis | 0 (0%) | 1 (2.3%) | 0 (0%) |
| | Cough caused by ACEI | 0 (0%) | 1 (2.3%) | 0 (0%) |
| Nervous system | Dizziness | 2 (4.9%) | 3 (6.8%) | 3 (7.9%) |
| | Insomnia | 2 (4.9%) | 1 (2.3%) | 0 (0%) |
| | Anxiety | 1 (2.4%) | 2 (4.5%) | 0 (0%) |
| | Blush | 0 (0%) | 1 (2.3%) | 0 (0%) |
| | Fullness of headache | 0 (0%) | 1 (2.3%) | 0 (0%) |
| | Sleepiness | 0 (0%) | 0 (0%) | 1 (2.6%) |
| | Dreaming | 1 (2.4%) | 0 (0%) | 0 (0%) |
| | Headache | 1 (2.4%) | 3 (6.8%) | 4 (10.5%) |
| Urinary tract system | Gallbladder infection | 1 (2.4%) | 0 (0%) | 0 (0%) |
| | Urinary tract infections | 0 (0%) | 0 (0%) | 1 (2.6%) |
| Skin | itch | 0 (0%) | 2 (4.5%) | 0 (0%) |
| | Rash | 1 (2.4%) | 1 (2.3%) | 0 (0%) |
| | Eye itching | 0 (0%) | 0 (0%) | 1 (2.6%) |
| | Intermittent bright eye | 1 (2.4%) | 0 (0%) | 0 (0%) |
| | Blurred vision | 1 (2.4%) | 0 (0%) | 0 (0%) |
| | Intermittent tinnitus | 0 (0%) | 1 (2.3%) | 0 (0%) |
| | Rib bruise | 1 (2.4%) | 0 (0%) | 0 (0%) |
| Eye and ear | Eye itching | 0 (0%) | 1 (2.3%) | 0 (0%) |
| | Intermittent bright eye | 0 (0%) | 1 (2.3%) | 0 (0%) |
| | Blurred vision | 0 (0%) | 1 (2.3%) | 0 (0%) |
| | Intermittent tinnitus | 0 (0%) | 1 (2.3%) | 0 (0%) |
| Biomarker | CRP | 2 (4.9%) | 1 (2.3%) | 3 (7.9%) |
| | Increased LP-PLA2 value | 1 (2.4%) | 1 (2.3%) | 2 (5.3%) |
| | Increased BNP value | 0 (0%) | 2 (4.5%) | 0 (0%) |
| Abnormal value of tested results in laboratory | Increased leukocyte esterase | 1 (2.4%) | 0 (0%) | 0 (0%) |
| | Increased creatinine | 0 (0%) | 1 (2.3%) | 1 (2.6%) |
| | Increased blood urea | 0 (0%) | 1 (2.3%) | 0 (0%) |
| | Slight prerenal azotemia | 0 (0%) | 1 (2.3%) | 0 (0%) |
| | AST increase | 0 (0%) | 2 (4.5%) | 0 (0%) |
| | ALT increase | 0 (0%) | 2 (4.5%) | 0 (0%) |
| | eGFR decrease | 0 (0%) | 0 (0%) | 2 (5.3%) |
| | (+++) urine protein | 0 (0%) | 0 (0%) | 1 (2.6%) |
| | Hyperglycemia | 0 (0%) | 1 (2.3%) | 0 (0%) |

*referred to the incidence ratio of ADRs in each group. There were totally 41 patients in the low dose group, 44 patients in the high dose group, and 38 patients in the placebo group.

Except three severe ADRs, most of the ADRs occurring in three groups were believed to be in mild or moderate degree. There was one patient with diabetic foot ulcer (uncorrelated) in the low dose group, one with headache (uncorrelated) in the high dose group, and one with intense chest pain (uncorrelated) in the placebo group.

The patients included in this study had complicated disease history, progressive disease and combined medication. By judgment, the treatment-related AE included:

Low dose group (5 cases): 1 case of mild dizziness; 1 case of mild diarrhea; 1 case of mild indigestion; 1 case of mild watery stool and 1 case of mild abdominal distension.

High dose group (3 cases): 1 case of mild intermittent blush, distending feeling in head and mild headache and palpitation; 1 case of mild abdominal distension and 1 case of mild watery stool.

Placebo group (4 cases): 1 case of mild dizziness and headache; 1 case of mild constipation; 1 case of mild indigestion and 1 case of mild sleepiness.

In the placebo group, low dose group and high dose group, the patients having symptoms of coronary heart disease (including shout breath, chest distress, chest pain or discomfort, angina pectoris) is 23.7%, 12.2% and 9.1%, respectively, which demonstrates that Dantonic® group has significant difference from placebo group, and has slight difference from low and high dose groups.

b) Death, Other SAE and Other Important AE

None of dearth case had been found in the Chinese medicine composition in US phase II clinical trial. As shown in table 13, said SAE in the trial was present as follows: 1 case of cardiovascular symptoms of chest pain, atrial fibrillation and acute myocardial infarction (AMI), 1 case of foot ulcer and 1 case of hyperglycemia. Said SAE in the treatment groups (high and low dose) of the Chinese medicine composition included 1 case of chest pain, 1 case of atrial fibrillation, 1 case of AMI, 1 case of foot ulcer and 1 case of hyperglycemia. Besides, there were 2 SAEs in the placebo group, displaying chest pain.

After being analyzed according to their disease history, none of SAE cases was correlated with the drug treatment. Eventually, the results of SAE were good (1 case improved and 6 cases solved completely). In the high dose group, the chest pain in 1 patient and the serious foot ulcer in another patient were believed to be more serious than other mild and moderate AEs. In addition, there were 3 patients who had withdrew from/early terminated the trial; they included 1 case of serious chest pain in the high dose group, 1 case of mild foot ulcer in the low dose group and 1 case of chest pain in the placebo group.

In summary, said symptoms in the study mainly belonged to mild and moderate AE, which was related to the patients' disease history, not related to drug treatment of the Chinese medicine composition.

TABLE 13

Summary of reported SAE

| Patient No. | Diagnosis | Severity degree | Adopted measures | Results | Correlation with the trial |
|---|---|---|---|---|---|
| 104 | Chest pain syndrome (after two times of baseline, before taking drug) | Severe | Withdrawal from the trial | Solved completely | Uncorrelated |
| 307 | AMI | Moderate | None | Solved completely | Uncorrelated |
| 401 | Foot ulcer (diabetics foot) | Mild | Hospitalized for diabetics foot | Improved | Uncorrelated |
| 413 | Atrial fibrillation | Moderate | Hospitalized | Solved completely | Uncorrelated |
| 806 | Chest pain syndrome (after two times of baseline, before taking drug) | Moderate | Hospitalized | Solved completely | Uncorrelated |

Summary of Safety

Most of the ADRs occurring in phase II clinical trial were mild and uncorrelated with the drug treatment. Compared with the placebo group, the AEs occurring in the group of Dantonic® only had mildly irritating effect on the digestive system, e.g. the feeling of abdominal distension. The appearance of slight blush was indication of the effect of improving blood circulation. It was confirmed in the study that the Chinese medicine composition was a clinically-used safe drug.

During the 18-month clinical trial, all of reported 5 cases of SAE were uncorrelated with the tested drug. Other AEs listed in disease category was seldom occurred either, or existed previously, e.g. cold, tooth pain and chest pain. By cross-comparison, the tested drug of the Chinese medicine composition had the same incidence ratio of AE with the placebo group. Accordingly, it was determined that the AE had nothing to do with the drug treatment.

I.1.11 Cardiac Safety

Figure 23:
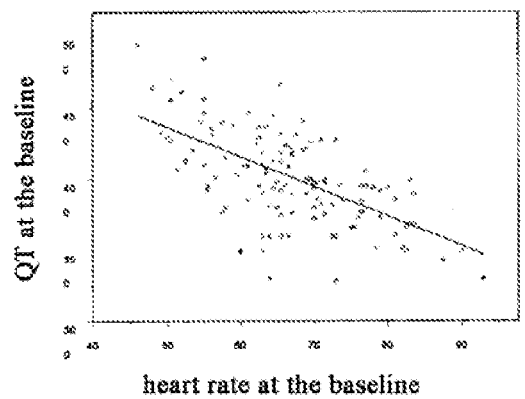
Figure 23:
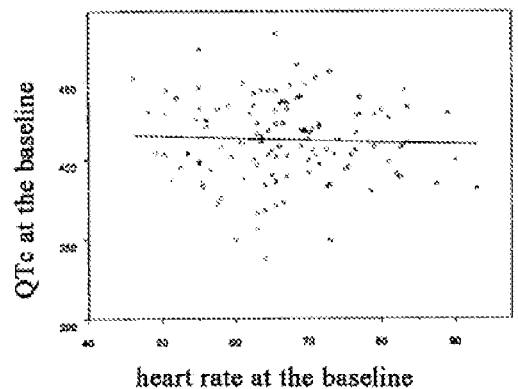
Figure 23:
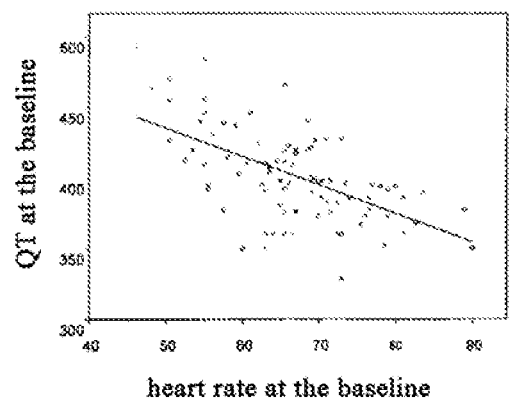
Figure 23:
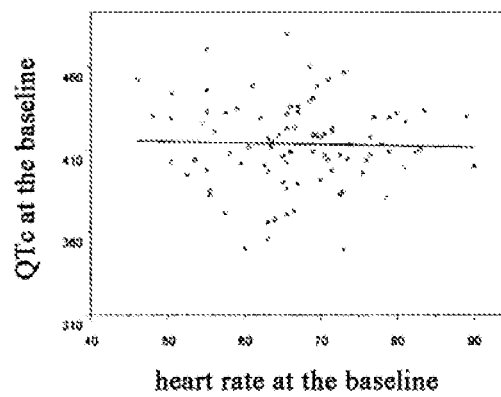

The QT interval showed an obvious correlation with heart rate (HR). QTc was determined by Frederica method, and consequently the QTc was independent with the HR (FIGS. 23$a$ and 23$b$). The average change of QTc in 2$^{nd}$ week, 4$^{th}$ week and 8$^{th}$ week was determined by 2 values above the baseline (Table 14). None of prolonged QTc was found in 2 treatment groups during period of drug treatment.

TABLE 14

Time-based change of QTc in all treatment groups (ITT and PPT population)

| Dataset | Groups | Time-based change of QTc | | |
|---|---|---|---|---|
| | | 14$^{th}$ day | 28$^{th}$/29$^{th}$ day | 56$^{th}$/57$^{th}$ day |
| ITT data | High dose group | 1.68 | −3.89 | 0.72 |
| | Low dose group | 0.56 | 0.19 | 0.14 |
| | Placebo group | 2.98 | −0.87 | −2.44 |
| PPT data | High dose group | 0.91 | 0.71 | 3.38 |
| | Low dose group | 0.66 | 0.69 | 0.04 |
| | Placebo group | 2.70 | −0.19 | −2.56 |

ILLUSTRATION OF DRAWINGS

FIG. 1 was the flow chart of T89-005-0003-US trial.

FIG. 2 showed the population statistics and baseline characteristics in the ITT analysis set.

FIG. 3 showed the population statistics and baseline characteristics in the PPT analysis set.

FIG. 4 depicted the change of the ITT analysis set population TED value in the valley level of ETT.

FIG. 5 depicted the change of the ITT analysis set population TED value in the peak level of ETT.

Figure 6:
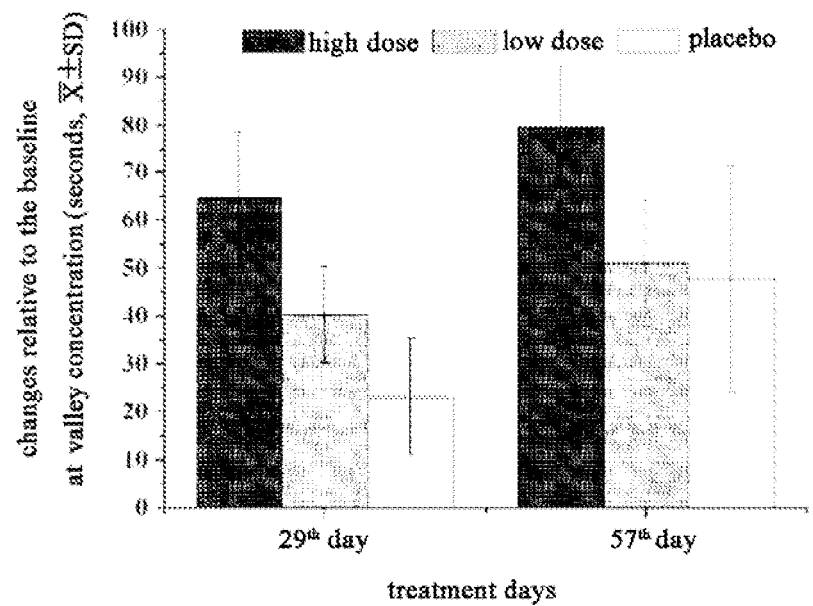

FIG. 6 showed the change of PPT analysis set population TED value relative to the baseline in the valley level of ETT.

Figure 7:
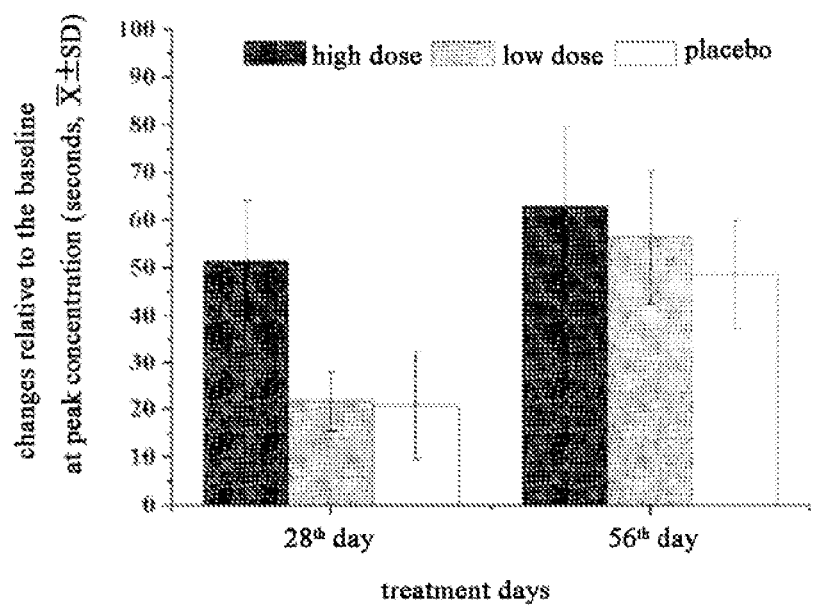

FIG. 7 showed the change of PPT analysis set population TED value relative to the baseline in the peak level of ETT.

Figure 8:
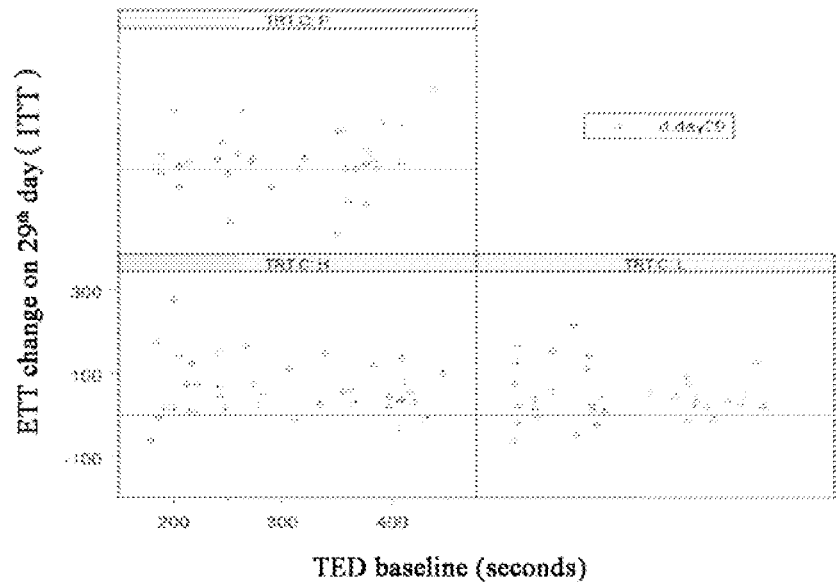
Figure 8:
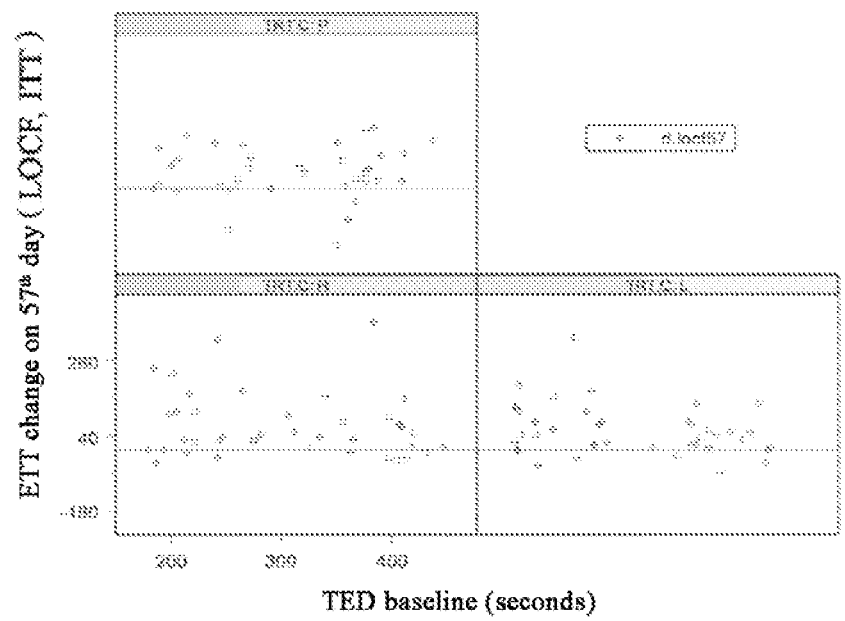
Figure 9:
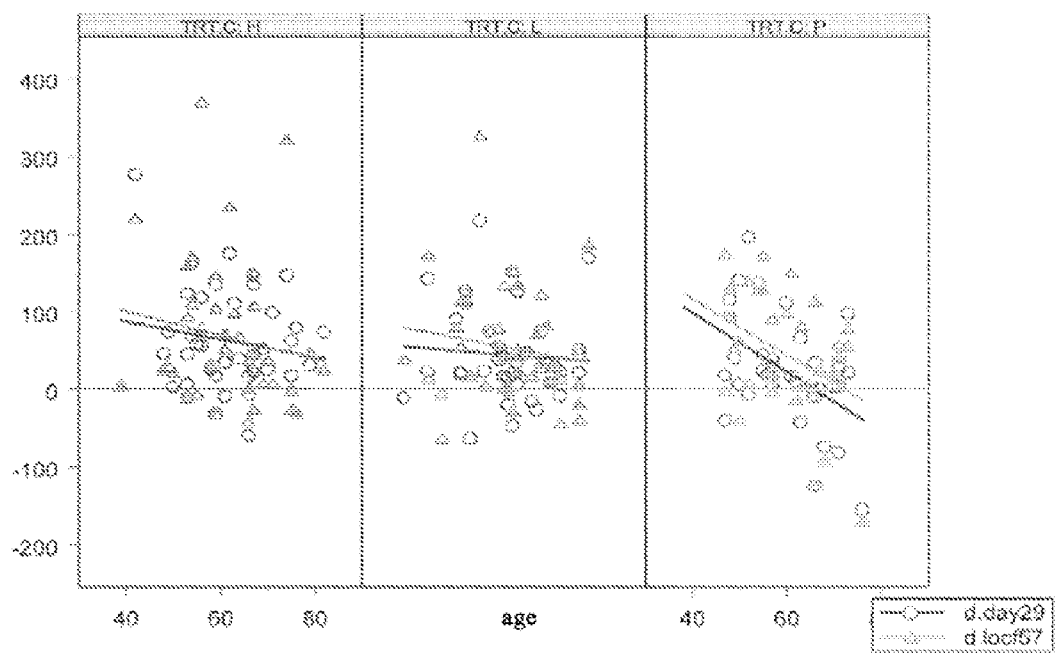

FIG. 8$a$-$b$ depicted the change of ITT analysis set population TED value in relative to different TED baseline during different period of time; FIG. 8$a$ depicted the change of ITT analysis set population TED value relative to different TED baseline in 29$^{th}$ day; and FIG. 8$b$ depicted the change of ITT analysis set population TED value in relative to different TED baseline on 57$^{th}$ day.

FIG. 9 showed the correlation between the change of ITT analysis set population and the age.

Figure 10:
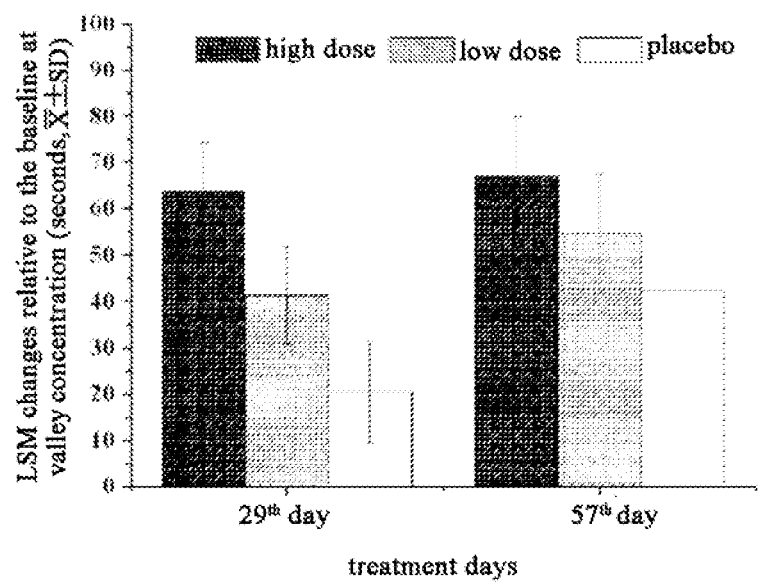
Figure 10:
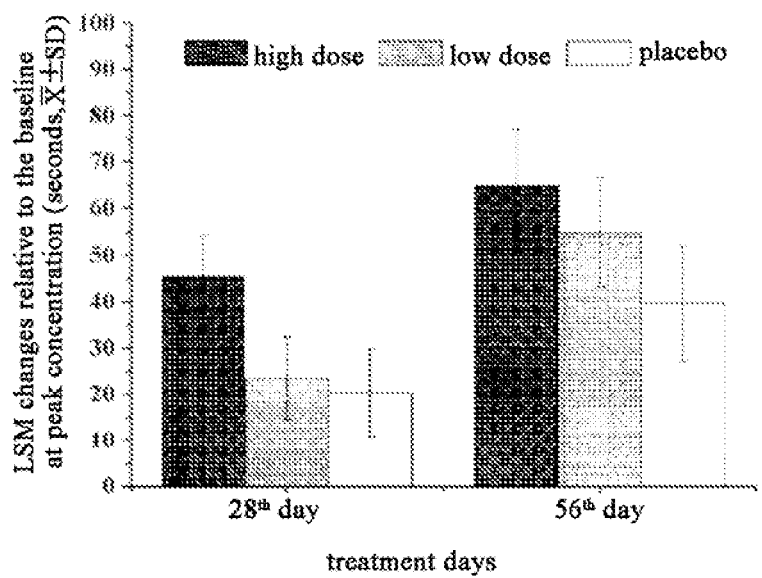

FIG. 10$a$-$b$ showed the analysis of LSM on the improvement of TED value relative to the baseline in the ITT analysis set population separately at peak and valley concentration; FIG. 10$a$ showed the analysis of LSM on the improvement of TED relative to the baseline in the ITT analysis set population at valley concentration; FIG. 10$b$ showed the analysis of LSM on the improvement of TED relative to the baseline in the ITT analysis set population at peak concentration.

Figure 11:
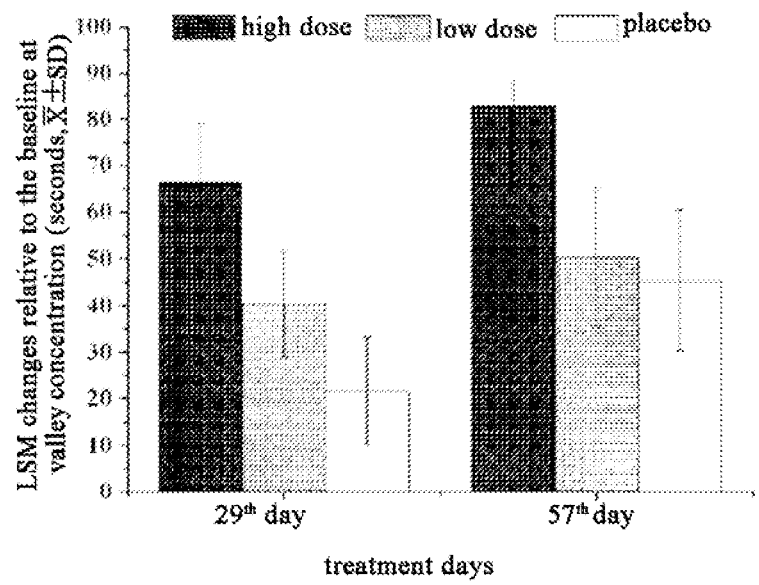
Figure 11:
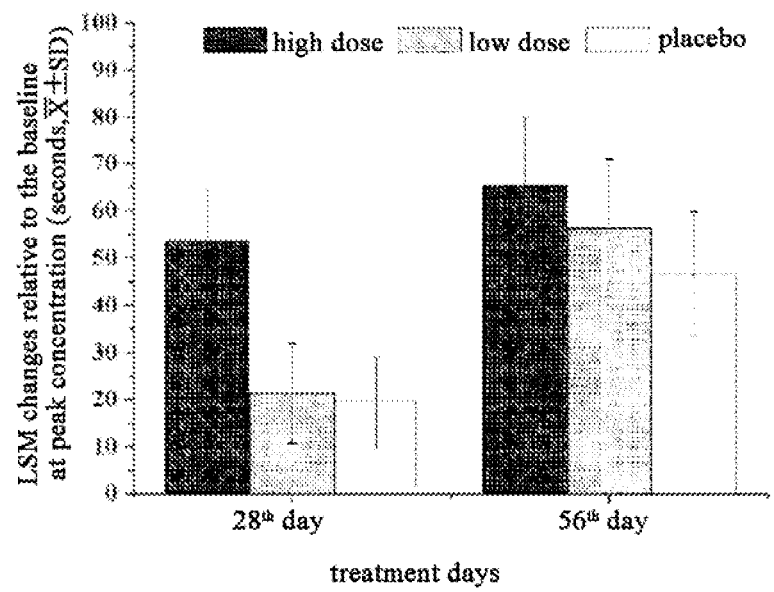

FIG. 11$a$-$b$ showed the analysis of LSM on the improvement of TED value relative to the baseline in the PPT analysis set population separately at peak and valley concentration; FIG. 11a showed the analysis of LSM on the improvement of TED relative to the baseline in the PPT analysis set population at valley concentration; FIG. 11b showed the analysis of LSM on the improvement of TED relative to the baseline in the PPT analysis set population at peak concentration.

FIG. 12a-b depicted the average change of weekly angina frequency relative to the baseline in the ITT and PPT analysis set population; FIG. 12a depicted the average change of weekly angina frequency relative to the baseline in the ITT analysis set population; FIG. 12b depicted the average change of weekly angina frequency relative to the baseline in the PPT analysis set population.

FIG. 13a-b depicted the average change of weekly nitroglycerin consumption relative to the baseline in the ITT and PPT analysis set population; FIG. 13a depicted the average change of weekly nitroglycerin consumption relative to the baseline in the ITT analysis set population; FIG. 13b depicted the average change of weekly nitroglycerin consumption relative to the baseline in the PPT analysis set population.

FIG. 14 depicted the improvement of the ITT analysis set population TCP in the valley level of ETT.

FIG. 15 depicted the improvement of ST-segment depression in different dose groups in the valley level of ETT.

FIG. 16 depicted the life quality changes over time in the ITT analysis set population.

FIG. 17 depicted the BNP change percentage relative to the baseline in the ITT analysis set population.

FIG. 18 depicted the Lp-PLA2 change percentage relative to the baseline in the ITT analysis set population.

FIG. 19 showed the correlation between the ETT change and the biochemical indices.

FIG. 20a-b depicted the change of TED value relative to the baseline in the populations of different ages; FIG. 20a depicted the change of TED value relative to the baseline in population (<64.5 years old); FIG. 20b depicted the change of TED value relative to the baseline in population (≥64.5 years old).

FIG. 21a-b depicted the change of TED value relative to the baseline in the populations of different baseline; FIG. 21a depicted the change of TED value relative to the baseline in the population (baseline<300 s); FIG. 21b depicted the change of TED value relative to the baseline in the population (baseline≥300 s).

FIG. 22 showed the number of the ITT analysis set population who missed taking capsule.

FIG. 23a-b analyzed the correlation between the QTc and the heart rate respectively in ITT and PPT analysis set population; FIG. 23a showed the correlation between the QTc and the heart rate in ITT analysis set population; FIG. 23b showed the correlation between the QTc and the heart rate in PPT analysis set population.

EMBODIMENTS

The present invention will be further described with reference to the following examples, which are solely used to illustrate the present invention without limitation.

Preparative Example 1

(1) Formulation

| | |
|---|---|
| Radix *Salvia Miltiorrhiza* | 45.0 g |
| Radix *Notoginseng* | 47.0 g |
| Borneol | 0.1 g |
| Adjuvant PEG-6000 | 18 g |

One thousand dripping pills were prepared.

(2) Extraction of *Radix salvia Miltiorrhiza* and *Radix Notoginseng*.

Coarsely-ground *Radix salvia Miltiorrhiza* (45.0 g) and *Radix Notoginseng* (47.0 g) were placed into an extraction tank, into which water with 5 times the weight of the *Radix salvia Miltiorrhiza* and *Radix Notoginseng* crude drugs was poured to decoct for 2 hours for the first time, after filtration, 4 times water was added to the drug residues to decoct for 1 hour for the second time. After filtration, the residues were discarded. After combination of the decoction, the solution was filtered and concentrated to obtain an extract in a ratio of the extract volume (L) to the weight (Kg) of the *Radix salvia Miltiorrhiza* and *Radix Notoginseng* crude drugs as 1:0.9~1.1. Then, 95% (v/v) ethanol was slowly added into the obtained extract solution to make a final ethanol content of 69~71% (v/v), and allowed to stand still for 12 hours to separate the supernatant, and the supernatant was filtered. The filtrate was concentrated by removing the ethanol to obtain an extract with a relative density of 1.32~1.40.

(3) Preparation of Product

Afore-mentioned *Radix salvia Miltiorrhiza* & *Radix Notoginseng* extract, *Borneol* and PEG-6000 (18 g) were well mixed and heated to the temperature of 85~90° C. After being melted for 20~120 min, the mixture was transferred to a dripping machine tank whose temperature was kept at 85~90° C. to drip into the liquid paraffin at 7~8° C. The pills were taken out and the liquid paraffin was removed to give the product.

(4) Characteristics of Product

The product was a red-brownish black round pill with the uniform size, same color, fragrance in smell and bitter in flavor. Pill weight was 25 mg±15%/pill and 3.34±15% mm in diameter.

Preparative Example 2

Coarsely-ground *Radix salvia Miltiorrhiza* (70.0 g) and *Radix Notoginseng* (13.7 g) were placed into an extraction tank, into which water with 5 times the weight of the *Radix salvia Miltiorrhiza* and *Radix Notoginseng* crude drugs was poured to decoct for 2 hours for the first time, after filtration, 4 times water was added to the drug residues to decoct for 1 hour for the second time. After filtration, the residues were discarded. After combination of the decoction, the solution was filtered and concentrated to obtain an extract in a ratio of the extract volume (L) to the weight (Kg) of the *Radix salvia Miltiorrhiza* and *Radix Notoginseng* crude drugs as 1:0.9~1.1. Then, 95% (v/v) ethanol was slowly added into the obtained extract solution to make a final ethanol content of 69~71% (v/v), and allowed to stand still for 12 hours to separate the supernatant, and the supernatant was filtered. The filtrate was concentrated by removing the ethanol to obtain an extract with a relative density of 1.32~1.40.

Aforementioned *Radix salvia Miltiorrhiza* & *Radix Notoginseng* extract, *Borneol* (0.8) and PEG-6000 (15.5 g) were well mixed and heated to the temperature of 85° C. After being mixed for 30 min, the mixture was transferred to a dripping machine tank whose temperature was kept at 80° C. to drip into the liquid paraffin at 7° C. The pills were taken out and the liquid paraffin was removed to give the product.

The product was a red-brownish round pill with the uniform size, smooth surface, fragrance in smell and bitter in flavor. Pill weight was 25 mg±15%/pill and 3.34±15% mm in diameter.

Preparative Example 3

| | |
|---|---|
| Radix *Salvia Miltiorrhiza* | 96.0 g |
| Radix *Notoginseng* | 1.0 g |
| Borneol | 3.0 g |
| Adjuvant PEG-6000 | 20 g |

The *Radix salvia Miltiorrhiza* and *Radix Notoginseng* were extracted and the product prepared by the same method as that in the Preparative Example 1 except that temperature of dripping machine was at 64° C. and the liquid paraffin at 0° C.

The product was a red-brownish round pill with the uniform size, smooth surface, fragrance in smell and bitter in flavor. Pill weight was 25 mg±15%/pill and 3.34±15% mm in diameter.

Preparative Example 4

| | |
|---|---|
| Radix *Salvia Miltiorrhiza* & Radix *Notoginseng* extract (prepared by a method of Example 1) | 18 g |
| Borneol | 3.0 g |
| Lactitol | 45 g |
| Pregelatinized starch | 20 g |

The lactitol and the pregelatinized starch were well mixed and placed into a dripping machine, into which the *Radix salvia Miltiorrhiza* & *Radix Notoginseng* extract and *Borneol* were added, fully homogenized and heated on the water bath until melting under 83° C. water bath temperature. Under the temperature of 70° C., the melted solution was dropped into the coolant of 0° C. methyl silicone oil at a speed of 35 pills per min. After being formed, the pills were cleaned by absorbent paper to suck up the methyl silicone oil adhering to the pill surface. The pills were dried at low temperature to give the product.

Aforementioned product was round and even with the uniform size, same color and no adhesion. Disintegration time limit of the pill was determined in accordance with the monograph of disintegration time limit of Chinese Pharmacopoeia (2000). The results showed that the average time of passing the screen without baffle was 3.96 min. The disintegration time limit met the requirement of Chinese Pharmacopoeia.

Preparative Example 5

| | |
|---|---|
| Radix *Salvia Miltiorrhiza* & Radix *Notoginseng* extract (prepared by a method of Example 1) | 22 g |
| Borneol | 1.5 g |
| Lactitol | 40 g |
| Arabic gum | 20 g |

The lactitol and the Arabic gum were well mixed and placed into a dripping machine, into which the *Radix salvia Miltiorrhiza* & *Radix Notoginseng* extract and *Borneol* were added, fully homogenized and heated on the water bath until melting under 85° C. water bath temperature. Under the temperature of 64° C., the melted solution was dropped into the coolant of 4° C. liquid paraffin at a speed of 40 pills per min. After being formed, the pills were cleaned by absorbent paper to suck up the liquid paraffin adhering to the pill surface. The pills were dried at low temperature to give the product.

Aforementioned product was round and even with the uniform size, same color and no adhesion. Disintegration time limit of the pill was determined in accordance with the monograph of disintegration time limit of Chinese Pharmacopoeia (2000). The results showed that the average time of passing the screen without baffle was 4.25 min. The disintegration time limit met the requirement of Chinese Pharmacopoeia.

Preparative Example 6

| | |
|---|---|
| Radix *salvia Miltiorrhiza* & Radix *Notoginseng* extract (prepared by a method of Example 1) | 18 g |
| Borneol | 1.2 g |
| Microcrystalline cellulose | 40 g |
| Talcum powder | 20 g |
| 3% Polyvinylpyrrolidone (PVP) ethanol solution | proper amount |

A conventional method was used to prepare tablets.

Preparative Example 7

| | |
|---|---|
| Radix *salvia Miltiorrhiza* & Radix *Notoginseng* extract (prepared by a method of Example 1) | 18 g |
| Borneol | 1.2 g |
| Gel | 50 g |
| Glycerol | 10 g |

A conventional method was used to prepare capsules.

Preparative Example 8

| | |
|---|---|
| Radix *salvia Miltiorrhiza* & Radix *Notoginseng* extract (prepared by a method of Example 1) | 18 g |
| Borneol | 1.2 g |
| Magnesium stearate | 30 g |
| Starch | 15 g |
| 3% Polyvinylpyrrolidone (PVP) ethanol solution | proper amount |

A conventional method was used to prepare granules.

Preparative Example 9

| | |
|---|---|
| Radix *salvia Miltiorrhiza* & Radix *Notoginseng* extract (prepared by a method of Example 1) | 18 g |
| Borneol | 1.2 g |
| Microcrystalline cellulose | 35 g |
| Starch | 10 g |
| 3% Polyvinylpyrrolidone (PVP) ethanol solution | proper amount |

A conventional method was used to prepare pills.

Preparative Example 10

| | |
|---|---|
| Radix *salvia Miltiorrhiza* & Radix *Notoginseng* extract (prepared by a method of Example 11) | 600 g |
| Borneol | 5 g |
| PEG-6000 | 2000 g |

The PEG-6000 was placed into a melting tank, heated 90° C. to pre-melt. The *Radix salvia Miltiorrhiza* & *Radix Notoginseng* extract was added and mixed well to form a solution. Frequency of pneumatic vibration drippers was adjusted to 50 Hz, and the temperature of the thermal room was preserved at 80° C. with steam jacket. The melting tank was ventilated by the air pump through the pipe, which made afore-mentioned even-melted solution flow to the dripper and drop into the cooling tunnel. Said cooling tunnel was vertical to the group. Cooling air was started to make cooling temperature to −20° C. The angle between the cooling air inlet and the horizontal plane was 45°, and the cooling air was circulated inside the cooling tunnel to cooling solidify the solution that was dropped from the dripper into a solid dripping pills, which was collected in a barrel through the outlet in the bottom end of the tunnel (method as disclosed in Example 1 of Chinese Pat. 200710060640.1).

Preparative Example 11

| (1) Formulation | |
| --- | --- |
| Radix *Salvia Miltiorrhiza* | 373 g |
| Radix *Notoginseng* | 73 g |
| Borneol | 5.0 g |
| Adjuvant PEG-6000 | 182.5 g |

One thousand capsules were prepared.

(2) Extraction of *Radix salvia Miltiorrhiza* and *Radix Notoginseng*.

Coarsely-ground *Radix salvia Miltiorrhiza* and *Radix Notoginseng* were placed into an extraction tank, into which 0.45% (w/w) sodium bicarbonate solution with 5 times the weight of the *Radix salvia Miltiorrhiza* and *Radix Notoginseng* crude drugs was poured to decoct for 2 hours for the first time, after filtration, 4 times water was added to the drug residues to decoct for 1 hour for the second time. After filtration, the residues were discarded. After combination of the decoction, the solution was filtered and concentrated to obtain an extract in a ratio of the extract volume (L) to the weight (Kg) of the *Radix salvia Miltiorrhiza* and *Radix Notoginseng* crude drugs as 1:0.9~1.3. Then, 95% (v/v) ethanol was slowly added into the obtained extract solution to make a final ethanol content of 70% (v/v), and allowed to stand still for 12~24 hours to separate the supernatant, and the supernatant was filtered. The filtrate was concentrated by removing the ethanol to obtain 62.5 g extract with a relative density of 1.32~1.40.

(3) Preparation of Product

Afore-mentioned *Radix salvia Miltiorrhiza* and *Radix Notoginseng* extract, *Borneol* and PEG-6000 were well mixed and heated to the temperature of 85° C. After being melted for 30 min, the mixture was transferred to a dripping machine tank whose temperature was kept at 90° C. to drip into the liquid paraffin at 10° C. The pills were taken out and the liquid paraffin was removed to load into the capsule to give the product.

(4) Characteristics of Product

The product was the capsule. The content was a red-brownish black round pill with the uniform size, same color, fragrance in smell and bitter in flavor. Capsule weight was 250 mg±15%/pill per capsule.

What is claimed is:

1. A method of secondary prevention of coronary heart disease in a subject diagnosed as grade II or grade III angina pectoris by the Canadian Cardiovascular Society, said method comprising administering to a subject in need thereof a Chinese medicine composition comprising *Radix salvia Miltiorrhiza* and *Radix Notoginseng* extract and *Borneol*, wherein the weight ratio of the *Radix salvia Miltiorrhiza* and Radix *Notoginseng* extract to the *Borneol* is (8-15):1, and wherein weight of *Salvia Miltiorrhiza* and *Radix Notoginseng* extract is the dry weight, and wherein said *Radix salvia Miltiorrhiza* and *Radix Notoginseng* extract is prepared by extracting *Radix salvia Miltiorrhiza* and *Radix Notoginseng* simultaneously.

2. The method according to claim 1, wherein said coronary heart disease is angina pectoris.

3. The method according to claim 1, wherein said coronary heart disease is stable angina pectoris.

4. The method of claim 1, wherein said secondary prevention is manifested in increased exercise tolerance.

5. The method of claim 1, wherein said secondary prevention is manifested in prolonged exercised time.

6. The method of claim 1, wherein said secondary prevention is manifested in delay of the ST-segment depression or prolongation of its interval in a subject with induced stable angina pectoris.

7. The method of claim 1, wherein said secondary prevention is manifested in delay of the onset of angina pectoris or prolongation of its interval in a subject with induced stable angina pectoris.

8. The method of claim 1, wherein said secondary prevention is manifested in decrease of nitroglycerin consumption.

9. The method of claim 1, wherein said secondary prevention is manifested in reduced frequency of angina pectoris.

10. The method of claim 1, wherein said secondary prevention is manifested in improved quality of life of a subject with stable angina pectoris.

11. The method of claim 1, wherein said composition is used in combination with β-receptor blocker(s).

12. The method of claim 1, wherein said secondary prevention is manifested in improvement of levels of one or more of the following biochemical parameters: B-type natriuretic peptide (BNP), C-reactive protein (CRP), lipoprotein phospholipase (Lp-PLA2) and homocysteine (HCY).

13. The method of claim 1, wherein said secondary prevention is manifested in decrease of occurrence or reoccurrence of severe vascular events.

14. The method of claim 13, wherein said severe vascular event is death.

15. The method of claim 13, wherein said severe vascular event is myocardial infarction.

16. The method of claim 13, wherein said severe vascular is ischemia shock.

17. The method of claim 13, wherein said severe vascular event is a situation in which coronary artery bypass grafting, percutaneous transluminal angioplasty and/or angiocardiography is/are required.

18. The method of claim 13, wherein said Chinese medicine composition is used in combination with antiplatelet agent(s).

19. The method of claim 18, wherein said antiplatelet agent is aspirin.

20. The method of claim 1, wherein the Chinese medicine composition comprises *Radix salvia Miltiorrhiza* and *Radix Notoginseng* extract and *Borneol* in a weight ratio of (9-10):1, wherein weight of *Radix salvia Miltiorrhiza* and *Radix Notoginseng* extract is the dry weight.

21. The method of claim 20, wherein said *Radix salvia Miltiorrhiza* and *Radix Notoginseng* extract is prepared by extracting *Radix salvia Miltiorrhiza* and *Radix Notoginseng* simultaneously, and weight ratio of crude drugs of *Radix salvia Mitiorrhiza* and *Radix Notoginseng*, which are used as starting materials, is (3-7):1.

22. The method of claim 1, wherein said weight ratio of crude drugs of *Radix salvia Miltiorrhiza* and *Radix Notoginseng*, which are used as starting materials, is (4-6):1.

23. The method of claim 22, wherein said weight ratio of crude drugs of *Radix salvia Miltiorrhiza* and *Radix Notoginseng*, which are used as starting materials, is 5:1.

24. The method of claim 23, wherein said crude drugs of *Radix salvia Miltiorrhiza* and *Radix Notoginseng* are extracted with weak alkali aqueous solution.

25. The method of claim 24, wherein said *Radix salvia Miltiorrhiza* and *Radix Notoginseng* extract is prepared by a method comprising:

a. extracting pulverized *Radix salvia Miltiorrhiza* and *Radix Notoginseng* with water or weak alkali aqueous solution for 2-3 times, in an amount of 4-8 times the weight of the *Radix salvia Miltiorrhiza* and *Radix Notoginseng* for each time; filtering, combining and properly concentrating the filtrate;

b. performing alcohol precipitation by adding high concentration alcohol into the concentrated solution to make a final alcohol concentration of 50-85% (v/v), standing still to perform precipitation, filtering the supernatant, recovering alcohol from the obtained supernatant and concentrating to give the extract.

26. The method of claim 25, wherein the Chinese medicine composition is further formulated into a dripping pill, wherein said dripping pill is composed of said Chinese medicine composition and an adjuvant, wherein said adjuvant is PEG-6000, and the weight ratio of said Chinese medicine composition to said adjuvant is (0.2-0.8):1.

27. The method of claim 26, wherein said adjuvant is PEG-6000, and the weight ratio of said medicament to said adjuvant is (0.29-0.7):1.

28. The method of claim 26, wherein said adjuvant is PEG-6000, and the weight ratio of said composition to said adjuvant is (0.5-0.6):1.

* * * * *